(12) United States Patent
Ballet et al.

(10) Patent No.: US 9,107,948 B2
(45) Date of Patent: Aug. 18, 2015

(54) COMPOUNDS FOR DIAGNOSING DISEASES ASSOCIATED WITH THE EXPRESSION OF MUC5AC

(75) Inventors: Sébastien Ballet, Paris (FR); Walter Gonzalez, Sevran (FR); Yannick Rossez, Faumont (FR)

(73) Assignee: Guerbet, Villepinte (FR)

( * ) Notice: Subject to any disclaimer, the term of this patent is extended or adjusted under 35 U.S.C. 154(b) by 0 days.

(21) Appl. No.: 13/993,975

(22) PCT Filed: Nov. 30, 2011

(86) PCT No.: PCT/EP2011/071427
§ 371 (c)(1),
(2), (4) Date: Jun. 13, 2013

(87) PCT Pub. No.: WO2012/079989
PCT Pub. Date: Jun. 21, 2012

(65) Prior Publication Data
US 2014/0127139 A1 May 8, 2014

(30) Foreign Application Priority Data

Dec. 14, 2010 (FR) .................................... 10 60497

(51) Int. Cl.
| | | |
|---|---|---|
| *A61K 49/00* | (2006.01) | |
| *A61K 47/48* | (2006.01) | |
| *A61K 49/04* | (2006.01) | |
| *A61K 49/14* | (2006.01) | |
| *A61K 49/18* | (2006.01) | |
| *A61K 51/04* | (2006.01) | |
| *A61K 51/08* | (2006.01) | |
| *B82Y 5/00* | (2011.01) | |

(52) U.S. Cl.
CPC ........... *A61K 49/14* (2013.01); *A61K 47/48084* (2013.01); *A61K 49/0017* (2013.01); *A61K 49/049* (2013.01); *A61K 49/186* (2013.01); *A61K 49/1842* (2013.01); *A61K 49/1866* (2013.01); *A61K 51/048* (2013.01); *A61K 51/0478* (2013.01); *A61K 51/0482* (2013.01); *A61K 51/08* (2013.01); *A61K 51/088* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 6,264,914 | B1 | 7/2001 | Klaveness et al. |
| 6,417,324 | B1 * | 7/2002 | Sallberg ................. 530/300 |
| 6,537,520 | B1 | 3/2003 | Rajopadhye et al. |
| 7,157,619 | B1 * | 1/2007 | Lassner et al. ............. 800/281 |
| 7,745,391 | B2 * | 6/2010 | Mintz et al. ............... 514/19.3 |
| 2004/0029114 | A1 * | 2/2004 | Mack et al. ................. 435/6 |
| 2004/0253181 | A1 | 12/2004 | Port et al. |
| 2005/0100963 | A1 | 5/2005 | Sato et al. |
| 2006/0018830 | A1 | 1/2006 | Cappelletti et al. |
| 2009/0208420 | A1 | 8/2009 | Briel et al. |

FOREIGN PATENT DOCUMENTS

| | | |
|---|---|---|
| WO | 01/60416 A2 | 8/2001 |
| WO | 02/26776 A2 | 4/2002 |
| WO | 02/085908 A1 | 10/2002 |
| WO | 03/011115 A2 | 2/2003 |
| WO | 03/062198 A1 | 7/2003 |
| WO | 03/086284 A2 | 10/2003 |
| WO | 2004/058275 A2 | 7/2004 |
| WO | 2006/031885 A2 | 3/2006 |
| WO | 2007/064175 A1 | 6/2007 |
| WO | 2007/095871 A2 | 8/2007 |
| WO | 2007/099289 A1 | 9/2007 |
| WO | WO 2010119362 A1 * | 10/2010 |

OTHER PUBLICATIONS

International Search Report and Written Opinion for corresponding PCT Application No. PCT/EP2011/071427 dated Mar. 15, 2012.
Deutscher, "Phage Display in Molecular Imaging and Diagnosis of Cancer", Chem. Rev., 2010, pp. 3196-3211, vol. 110, No. 5.
Kelly et al., "Isolation of a Colon Tumor Specific Binding Peptide Using Phage Display Selection", Neoplasia, Sep./Oct. 2003, pp. 437-444, vol. 5, No. 5.
Hsiung et al., "Detection of Colonic Dysplasia in vivo Using a Targeted Heptapeptide and Confocal Microendoscopy", Nature Medicine, Apr. 2008, pp. 454-458, vol. 14, No. 4.
Liu et al., "Comparitive Evaluation of Three 64Cu-Labeled E. coli Heat-Stable Enterotoxin Analogues for PET Imaging of Colorectal Cancer", Bioconjugate Chem., 2010, pp. 1171-1176, vol. 21, No. 7.
Li et al., "A Novel Peptide Specifically Targeting the Vasculature of Orthotopic Colorectal Cancer for Imaging Detection and Drug Delivery", Journal of Controlled Release, 2010, pp. 292-302, vol. 148, No. 3.
Kelly et al., "Detection of Invasive Colon Cancer Using a Novel, Targeted, Library-Derived Fluorescent Peptide", Cancer Research, Sep. 1, 2004, pp. 6247-6251, vol. 65, No. 17.
Byrd et al., "Mucins and Mucin Binding Proteins in Colorectal Cancer", Cancer and Metastasis Reviews, 2004, pp. 77-99, vol. 23, No. 1-2.
Forgue-Lafitte et al., "Abnormal Expression of M1/MUC5AC Mucin in Distal Colon of Patients with Diverticulitis, Ulcerative Colitis and Cancer", Int. J. Cancer, 2007, pp. 1543-1549, vol. 121, No. 7.
Lee et al., "Peptides and Peptide Hormones for Molecular Imaging and Disease Diagnosis", Chem. Rev., 2010, pp. 3087-3111, vol. 110, No. 5.
Gouyer et al., "Specific Secretion of Gel-Forming Mucins and TFF Peptides in HT-29 Cells of Mucin-Secreting Phenotype", Biochimica et Biophysica, 2001, pp. 71-84, vol. 1539.
Pecora, "Dynamic Light Scattering Measurement of Nanometer Particles in Liquids", Journal of Nanoparticle Research, 2000, pp. 123-131, vol. 2.
Sheehan et al., "Physical Characterization of the MUC5AC Mucin: A Highly Oligomeric Glycoprotein Whether Isolated from Cell Culture or In Vivo From Respiratory Mucous Secretions", Journal of Biochemistry, 2000, pp. 37-44, vol. 347.

\* cited by examiner

*Primary Examiner* — Julie Ha
*Assistant Examiner* — Kristina M Hellman
(74) *Attorney, Agent, or Firm* — Thompson Coburn LLP

(57) ABSTRACT

The application relates to a compound of general formula (I) below:

Signal-Linker-Peptide                (I)

and to the uses thereof for medical imaging or diagnosis or the preparation of a composition for diagnosis of an MUC5AC pathological condition.

20 Claims, 6 Drawing Sheets

SEQUENCE LISTING

<160> NUMBER OF SEQ ID NOS: 5

<210> SEQ ID NO 1

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is either absent or represents Cys or Met
<220> FEATURE:
<221> NAME/KEY: MISC_FEATURE
<222> LOCATION: (2)..(2)
<223> OTHER INFORMATION: Xaa = Hydroxyproline or Pro
<220> FEATURE:
<221> NAME/KEY: MISC_FEATURE
<222> LOCATION: (3)..(3)
<223> OTHER INFORMATION: Xaa = Thr or Ser
<220> FEATURE:
<221> NAME/KEY: MISC_FEATURE
<222> LOCATION: (4)..(4)
<223> OTHER INFORMATION: Xaa = Ile or Leu or Val
<220> FEATURE:
<221> NAME/KEY: MISC_FEATURE
<222> LOCATION: (5)..(5)
<223> OTHER INFORMATION: Xaa = Tyr or Phe or Trp
<220> FEATURE:
<221> NAME/KEY: MISC_FEATURE
<222> LOCATION: (6)..(6)
<223> OTHER INFORMATION: Xaa = Hydroxyproline or Pro
<220> FEATURE:
<221> NAME/KEY: MISC_FEATURE
<222> LOCATION: (7)..(7)
<223> OTHER INFORMATION: Xaa = Ile or Leu or Val
<220> FEATURE:
<221> NAME/KEY: MISC_FEATURE
<222> LOCATION: (8)..(8)
<223> OTHER INFORMATION: Xaa = Ile or Leu or Val
<220> FEATURE:
<221> NAME/KEY: MISC_FEATURE
<222> LOCATION: (9)..(9)
<223> OTHER INFORMATION: Xaa is either absent or represents Cys or Met

<400> SEQUENCE: 1

Xaa Xaa Xaa Xaa Xaa Xaa Xaa Xaa Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Cys Pro Ser Ile Tyr Pro Leu Leu Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Pro Ser Ile Tyr Pro Leu Leu
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is either absent or represents Cys or Met
<220> FEATURE:
<221> NAME/KEY: MISC_FEATURE
<222> LOCATION: (2)..(2)
<223> OTHER INFORMATION: Xaa = Ile or Leu or Val or Ala
<220> FEATURE:
<221> NAME/KEY: MISC_FEATURE
<222> LOCATION: (3)..(3)
<223> OTHER INFORMATION: Xaa = Thr or Ser
<220> FEATURE:
<221> NAME/KEY: MISC_FEATURE
<222> LOCATION: (4)..(4)
<223> OTHER INFORMATION: Xaa = Ile or Leu or Val
<220> FEATURE:
<221> NAME/KEY: MISC_FEATURE
<222> LOCATION: (5)..(5)
<223> OTHER INFORMATION: Xaa = Hydroxyproline or Pro
<220> FEATURE:
<221> NAME/KEY: MISC_FEATURE
<222> LOCATION: (6)..(6)
<223> OTHER INFORMATION: Xaa = Hydroxyproline or Pro
<220> FEATURE:
<221> NAME/KEY: MISC_FEATURE
<222> LOCATION: (7)..(7)
<223> OTHER INFORMATION: Xaa = Ile or Leu or Val
<220> FEATURE:
<221> NAME/KEY: MISC_FEATURE
<222> LOCATION: (8)..(8)
<223> OTHER INFORMATION: Xaa = Ile or Leu or Val
<220> FEATURE:
<221> NAME/KEY: MISC_FEATURE
<222> LOCATION: (9)..(9)
<223> OTHER INFORMATION: Xaa is either absent or represents Cys or Met

<400> SEQUENCE: 4

Xaa Xaa Xaa Xaa Xaa Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Cys Ala Leu Ile Pro Pro Leu Leu Cys
1               5
```

COMPOUNDS FOR DIAGNOSING DISEASES ASSOCIATED WITH THE EXPRESSION OF MUC5AC

CROSS-REFERENCE TO RELATED APPLICATIONS

This application is a National Stage application of International Patent Application No. PCT/EP2011/071427, filed on Nov. 30, 2011 which is incorporated by reference herein in its entirety, which claims the benefit of French Application No. 10 60497 filed Dec. 14, 2010, which is incorporated by reference herein in its entirety.

INCORPORATION OF SEQUENCE LISTING

A text file of the Sequence Listing contained in the file named "BET13P0776_Sequences_ST25.txt" which is 2,573 bytes (measured in MS-Windows®) in size and which was created on Jun. 12, 2013, is electronically filed herewith and is incorporated by reference in its entirety. This sequence listing consists of SEQ ID NO: 1-5.

BACKGROUND OF THE INVENTION

The invention relates to novel compounds for diagnosing diseases related to MUC5AC expression, to the process for preparing same and to the use thereof in medical imaging. Colorectal cancer is characterized by a loss of differentiation of the cells which form the glands of Lieberkühn. These glands lining the wall of the digestive tract are responsible for the synthesis of mucus, the major components of which are mucins. Mucins constitute a vast family of O-glycoproteins encoded by the MUC genes. They are very heterogeneous compounds, which have a high molecular weight and are very rich in sugars (up to 85% of the total weight). They are formed from a peptide axis which can be bristling with several hundred different glycan chains. Intestinal mucins perform a lubricant role and protect the epithelium against mechanical attacks associated with the digestion process. By means of their glycan chains, they establish numerous interactions with microorganisms, thus making it possible to maintain a rich and diversified bacterial flora, while at the same time preventing the proliferation of pathogenic strains. It has in fact been proposed that the various oligosaccharides constitute a mosaic of potential receptors capable of trapping numerous microorganisms in the layer of mucous while thus preventing infection of the underlying epithelium.

Numerous studies have demonstrated abnormalities in expression and modifications of glycosylation of mucins in patients suffering from colon cancer which are thought to influence cell growth, differentiation, transformation, adhesion and invasion of tumor cells. The MUC2 glycoprotein is the major mucin from the small intestine to the rectum. Its expression and that of MUC3 are greatly decreased in certain colorectal adenomas, whereas de novo expression of MUC5AC can be observed.

Under physiological conditions, MUC5AC is present in the respiratory pathways and the gastric and genital mucosa and is not present in healthy colonic mucosa. On the other hand, it is adamantly expressed by certain colorectal tumors and precancerous lesions. Thus, villous tumors which are not very dysplastic react positively to anti-MUC5AC antibodies, but the expression of this mucin decreases when the grade of dysplasia increases, and disappears completely when the tumor transforms into an adenocarcinoma. It has, moreover, been shown that 60% of "conventional" (tubular and villous) adenomas carry MUC5AC, compared with 100% of serrated adenomas and hyperplastic polyps.

All these data indicate that MUC5AC is an early marker for cancer transformation in the colonic mucosa.

Still today, one patient out of two suffering from colon cancer dies in France and it is the stage of progression of the tumor at the time of the diagnosis which is determining for the prognosis. Few diagnostic methods for colorectal cancer exist, since only colonoscopy and the search for hemoglobin in the feces are used. Colonoscopy is currently the screening method of choice, but it is an examination reputed to be painful and therefore often poorly accepted. This is all the more so since it does not make it possible to detect flat or sessile neoplastic polyps which are, by definition, not very visible and therefore often missed during a conventional endoscopic examination. As for examination of the feces, it only rarely enables the discovery of adenomas, even at an advanced stage, and does not therefore lend itself to the prevention of the development of cancer. Consequently, imaging modes known to those skilled in the art are advantageous alternatives, such as MRI, X-rays, gamma-ray scintigraphy, CT scan, ultrasound, PET and optical imaging. It is recalled that, in the case of MRI, a contrast is obtained through the administration of contrast agents containing paramagnetic or superparamagnetic metals which have an effect on the relaxivity of the water protons. In the case of scintigraphy, the contrast is obtained by specific localization of a radiopharmaceutical compound emitting γ or β rays.

Compounds of which the chemical synthesis is not too complex, which are sufficiently stable in vivo for use in medical imaging and the cost price of which is not too high are sought, in particular for MRI.

The applicant has succeeded in obtaining compounds which specifically target the MUC5AC mucin, and which are very advantageous for diagnostic imaging. In particular, the applicant has obtained favorable results in particular in vitro on the purified mucin, on cells in culture and on histological sections. Peptides have been selected for recognizing MUC5AC regardless of its glycosylation and, without being markers of other mucins such as MUC2 which are glycoproteins that are very structurally similar.

The effective compounds have at the same time enough affinity to recognize the target, strong specificity so as to be a distinctive indicator of the pathological condition and appropriate stability so as not to be degraded or modified in vivo; and in addition without the signal component attached to the peptide interfering in a bothersome manner with these various parameters (affinity and stability in particular).

After numerous attempts, the applicant has succeeded in obtaining effective compounds. The invention thus relates to a compound of general formula (I) below:

Signal-Linker-Peptide        (I)

in which:
  Signal represents a signal entity;
  Linker, which may or may not be present, represents a chemical linking component, and
  Peptide represents a peptide comprising an MUC5AC-targeting peptide (more exactly, a peptide component comprising or constituted by at least one MUC5AC-targeting peptide), the MUC5AC-targeting peptide being chosen from the peptides having the following formula, and the functional equivalents thereof:
  a) X1-X2-X3-X4-X5-X6-X7-X8-X9 (1) (SEQ ID No. 1) with:
    X1 absent or chosen from cysteine or methionine,
    X2 chosen from hydroxyproline or proline, X3 chosen from threonine or serine,
X4 chosen from isoleucine, leucine or valine,
X5 chosen from tyrosine, phenylalanine or tryptophan,
X6 chosen from hydroxyproline or proline,
X7 chosen from isoleucine, leucine or valine,
X8 chosen from isoleucine, leucine or valine,
X9 absent or chosen from cysteine or methionine,
preferably, the peptide CPSIYPLLC (SEQ ID No. 2) (Cys-Pro-Ser-He-Tyr-Pro-Leu-Leu-Cys) and the peptide PSIYPLL (SEQ ID No. 3);
b) X10-X11-X12-X13-X14-X15-X16-X17-X18 (2) (SEQ ID No. 4) with:
X10 absent or chosen from cysteine or methionine,
X11 chosen from isoleucine, leucine, valine or alanine,
X12 chosen from threonine or serine.
X13 chosen from isoleucine, leucine or valine,
X14 chosen from hydroxyproline or proline,
X15 chosen from hydroxyproline or proline,
X16 chosen from isoleucine, leucine or valine,
X17 chosen from isoleucine, leucine or valine,
X18 absent or chosen from cysteine or methionine;
c) CALIPPLLC (SEQ ID No. 5);
preferably, the peptide CALIPPLLC (SEQ ID No. 5) (Cys-Ala-Leu-He-Pro-Pro-Leu-Leu-Cys); the pharmaceutically acceptable salts of these compounds of a) or of b).

The expression "MUC5AC-targeting peptide" is also denoted MUC5AC PEPTIDE in the application. Advantageously, Peptide represents an MUC5AC PEPTIDE.

Advantageously, the Peptide (peptide comprising an MUC5AC PEPTIDE) according to the invention comprises at most 20 amino acids, advantageously at most 15 amino acids, advantageously at most 10 amino acids and advantageously 5 to 10 amino acids.

The expression "peptide CPSIYPLLC (SEQ ID No. 2) and peptide PSIYPLL (SEQ ID No. 3) and functional equivalents thereof" is intended to mean the peptide CPSIYPLLC (SEQ ID No. 2) and the peptide PSIYPLL (SEQ ID No. 3), the effectiveness of which has been demonstrated by the applicant, and the derived peptides of formula X1-X2-X3-X4-X5-X6-X7-X8-X9 (1) (SEQ ID No. 1) which, once included in the compound (I), exhibit an effectiveness in imaging that is similar to or better than CPSIYPLLC (SEQ ID No. 2) (which includes the peptidomimetics), this effectiveness being tested using in vitro tests and models described in detail in the application or suitable analogous models. The peptide CPSIYPLLC (SEQ ID No. 2) studied is a cyclic peptide and is exemplified in detail in the application.

Likewise, the expression "CALIPPLLC (SEQ ID No. 5) and functional equivalents thereof" is intended to mean the peptide CALIPPLLC (SEQ ID No. 5), the effectiveness of which has been demonstrated by the applicant, and the effective derived peptides of formula X10-X11-X12-X13-X14-X15-X16-X17-X18 (2) (SEQ ID No. 4). The peptide CALIPPLLC (SEQ ID No. 5) studied is a cyclic peptide and is exemplified in detail in the application.

In particular, a derivative of the peptide CPSIYPLLC (SEQ ID No. 2) and the peptide PSIYPLL (SEQ ID No. 3) includes a peptide or compound in which the sequence PSIYPLL (SEQ ID No. 3) constituting the sequence has been modified by addition, deletion, substitution or modification of at least one amino acid.

The substitution may be conservative or nonconservative. The substitution is conservative when an amino acid is substituted with an amino acid having similar properties (for example, polarity, hydrogen bonding potential, acidity, basicity, hydrophobicity, presence of an aromatic group, etc). A natural amino acid can be replaced with an unnatural amino acid, such as an amino acid in D configuration, a beta-amino acid or a gamma-amino acid. The MUC5AC PEPTIDE is, for example, modified using appropriate methodologies described in the prior art, for example in US2005100963 (columns 20-21, paragraphs [529] to [541] in the case of peptides targeting KDR receptors), in order to select effective compounds (I).

In the case of CPSIYPLLC (SEQ ID No. 2) and PSIYPLL (SEQ ID No. 3),

P, proline, can be replaced with another amino acid bearing a heterocycle, for example hydroxyproline or histidine, S, serine, can be replaced with another amino acid bearing a hydroxyl group, for example threonine or homoserine, I, isoleucine, can be replaced with other aliphatic amino acids (leucine, valine) or derivatives, for example substituted with alkyls, Y, tyrosine, can be replaced with other aromatic amino acids, in particular tryptophan or phenylalanine, L, leucine, can be replaced with other aliphatic amino acids (isoleucine, valine).

The sequence PSIYPLL (SEQ ID No. 3) can be modified by replacing one or more amide bonds with a bond which confers increased stability in vivo, for example which confers increased resistance to proteolysis.

The expression "peptide comprising at least one MUC5AC-targeting peptide" is intended to mean a peptide which has this peptide sequence for recognition of the biological target, optionally flanked, at the N-terminal and/or C-terminal end, by a chemical group which does not interfere with the effectiveness of this sequence in imaging.

The term "Signal" or "signal entity" is intended to mean a chemical entity which makes it possible to obtain, in medical imaging, in particular:

a chelate capable of being coupled to a paramagnetic metal, a metal nanoparticle, in particular a superparamagnetic nanoparticle of iron oxide, a lipid nanoparticle, advantageously in the form of an emulsion, this nanoparticle bearing at least one chelate capable of being coupled to a paramagnetic metal (in this case, the peptide is grafted to the lipid nanoparticle in an emulsion which is itself carrying chelates; the bonding of the peptide to the lipid nanoparticle is carried out, for example, via a chemical linking group).

In formula I, the expression "chemical linking component" is intended to mean one or more bonding groups or linkers L, i.e. a chemical group:

which makes it possible to link the Signal and the MUC5AC PEPTIDE peptide component, which does not itself have the signal entity function which is provided by the signal, which does not itself have the targeting function which is provided by the MUC5AC PEPTIDE.

According to one embodiment, the signal entity comprises a chelate (in complexed form or in a form complexed with a metal M). Advantageously, the chelate is coupled to the metal M. A large number of chelates, preferably macrocyclic chelates, are usable, in particular having the following formula (illustration with gadolinium Gd, other lanthanides also being suitable)

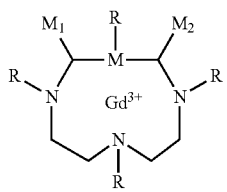

wherein:
M-M1-M2 forms a pyridine ring,
or M1 and M2 are absent and M represents a bond,
or M is N—R and M1 and M2 represent a hydrogen atom or a methyl,
wherein R is chosen independently from $CH_2CO_2$— or H or CHX—$CO_2$—, with at least one R being $CHXCO_2$— and X being L-B.

Use may in particular be made of a macrocyclic chelate among 1,4,7,10-tetraazacyclododecane-1,4,7,10-tetraacetic acid (DOTA), 1,4,7,10-tetraazacyclododecane-1,4,7-triacetic acid (DO3A), 10-(2-hydroxypropyl)-1,4,7,10-tetraazacyclododecane-1,4,7-triacetic acid (HPDO3A), (MCTA), (DOTMA) and 3,6,9,15-tetraazabicyclo[9.3.1]pentadeca-1(15),11,13-triene-3,6,9-triacetic acid (PCTA).

Use may also be made of derivatives in which one or more carboxylic groups are in the form of a corresponding salt, ester or amide; or a corresponding compound in which one or more carboxylic groups are replaced with a phosphonic and/or phosphinic group.

Use may also be made of a chelate among: DOTA gadofluorines, DO3A, HPDO3A, TETA, TRITA, HETA, DOTA-NHS, M4DOTA, M4DO3A, PCTA and BOPTA, and derivatives thereof. More broadly, the chelate(s) forming the signal entity may correspond to the formula of document WO 01/60416 or WO 03/062198 (pages 23 to 25).

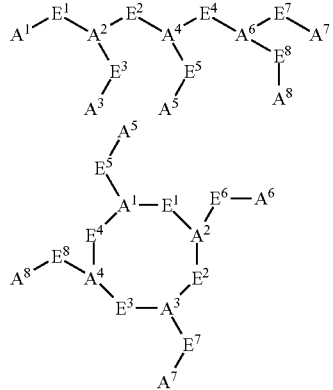

Use may in particular be made of the compounds DOTA, NOTA, DO3A, AAZTA and HOPO, and also the known multimers and derivatives thereof, in particular:

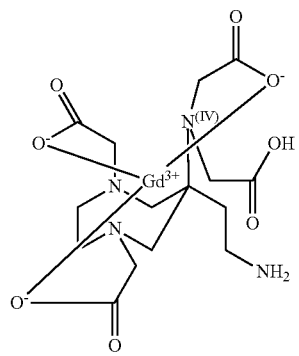

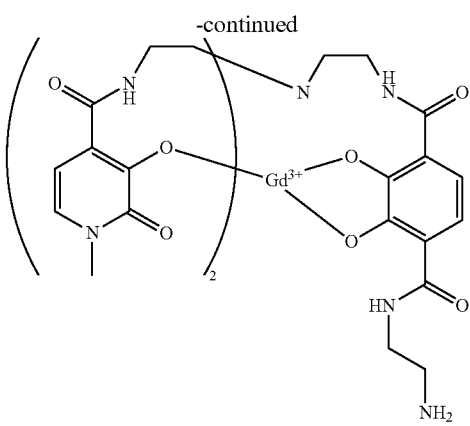

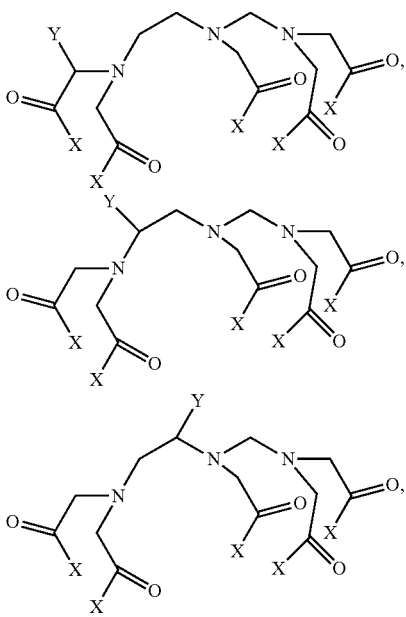

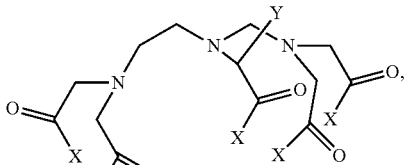

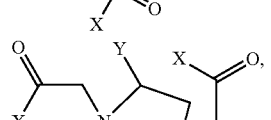

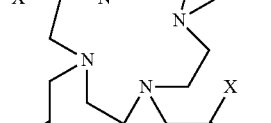

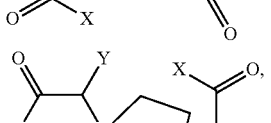

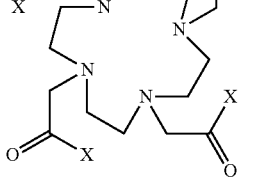

-continued

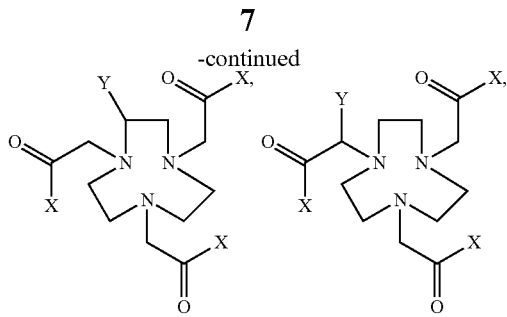

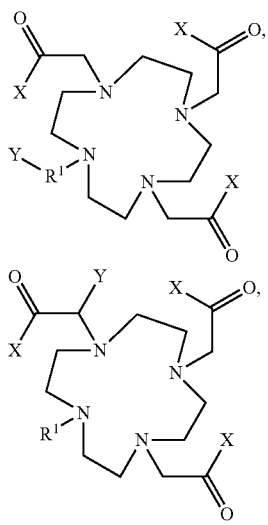

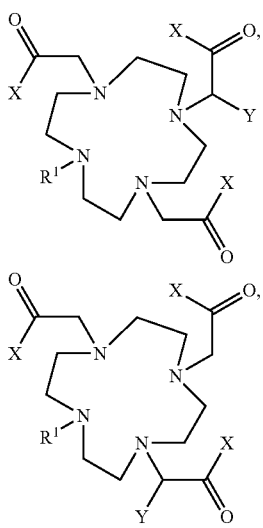

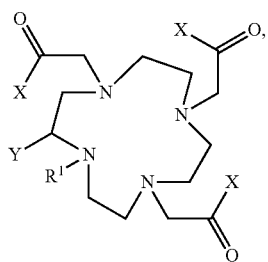

-continued

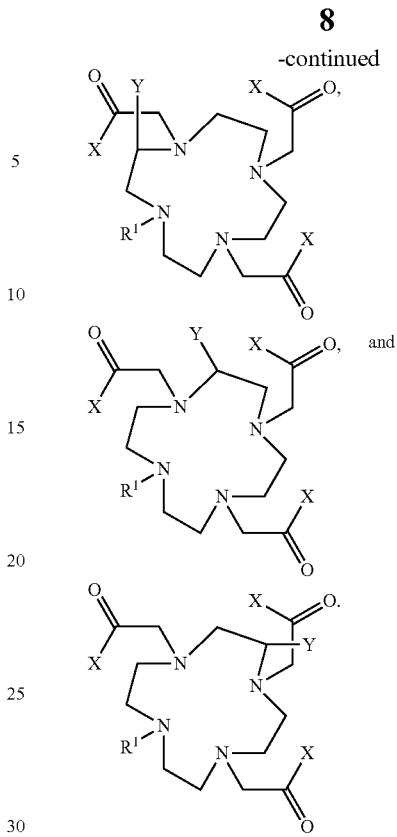

The coupling of chelates with biovectors, in particular peptide biovectors, is described in the prior art, and generally involves a chemical linking (Linker) as described, for example, in document WO 01/60416.

The structure and the chemical nature of the chemical linking component are defined so as to enable chemical coupling between, on the one hand, the MUC5AC PEPTIDE peptide component and, on the other hand, the Signal entity (the chelate(s) used), and in such a way as to obtain affinity of the MUC5AC PEPTIDE component for its target and recognition specificity appropriate for the use.

Advantageously, the metal M is a paramagnetic metal ion, or a radionuclide. The complex formed by the chelate and the metal M is stable under physiological conditions in such a way as to avoid undesired release of the metal M in the organism. Advantageously, the signal entity (chelate) comprises at least one functional group which makes it possible to link the signal entity with the linker (the chemical linking component described in the application) or directly with the Peptide. The invention also relates to the compounds of formula (I) in which the chelate is not complexed with the metal.

A large number of Linkers between the chelate(s) and the MUC5AC PEPTIDE(S) can be used, insofar as they are capable of interacting with at least one peptide functional group and at least one chelate functional group.

Advantageously, the chemical linking group or linker L is chosen from the following:

a) a group of formula Q1-l-Q2, in which Q1 and Q2, which may be identical or different, represent O, S, NH, $CO_2$, —NHCO, CONH, NHCONH, NHCSNH, $SO_2NH$— or $NHSO_2$—, and l represents an alkyl (advantageously $C_1$-$C_{10}$) group, alkoxyalkyl (advantageously $C_1$-$C_{10}$) group, alkenyl (advantageously $C_2$-$C_6$) group, alkynyl (advantageously $C_2$-$C_6$) group or polyalkoxyalkylene group, or an alkyl group interrupted with one or more squarates, with one or more aryls, advantageously phenyl, or with one or more groups chosen from —NH—, —O—, —CO—, —NH(CO)—, —(CO)NH—, —O(CO)—, or —(OC)O—;

b) a group $(CH_2)_n$, $(CH_2)_n$—CO—, —$(CH_2)_n$NH—CO— with n=1 to 10, $(CH_2CH_2O)_q(CH_2)_r$—CO—, $(CH_2CH_2O)_q(CH_2)_r$—NH—CO— with q=1-10 and r=1-10, $(CH2)n$—CONH—, $(CH_2)_n$—CONH—PEG, $(CH2)_n$—, squarate,

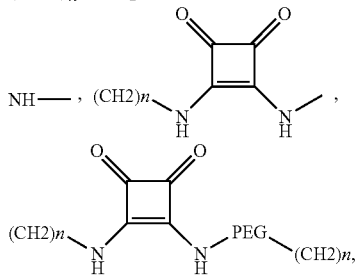

$(CH_2)_n$-squarate-$(CH_2CH_2O)_q(CH_2)_r$—CO with n=1 to 5 and advantageously n=3, 4 or 5, HOOC—$CH_2$—O—$(CH_2)_2$—O—$CH_2$—COOH; HOOC—$(CH_2)_2$—$CO_2$—$(CH_2)_2$—OCO—$(CH_2)_2$—COOH; HOOC—CH(OH)—CH(OH)—COOH; HOOC—$(CH_2)_n$—COOH; $NH_2(CH_2)$n-$NH_2$, with n=1-20; $NH_2$—$(CH_2)_n$—$CO_2H$; $NH_2$—$CH_2$$(CH_2$—O—$CH_2)_n$—$CO_2H$ with n=1 to 10.

In particular:

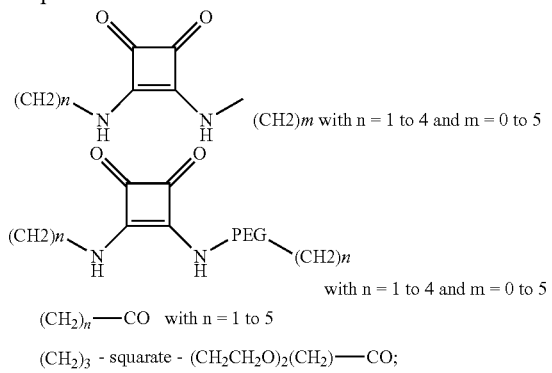

$(CH_2)_n$—CO with n = 1 to 5

$(CH_2)_3$ - squarate - $(CH_2CH_2O)_2(CH_2)$—CO;

c) linkers described in patent U.S. Pat. No. 6,264,914, capable of reacting with the amino, hydroxyl, sulfhydryl, carboxyl, carbonyl, carbohydrate, thioester, 2-aminoalcohol, 2-aminothiol, guanidyl, imidazolyl and phenolic functional groups (of the biovectors and of the chelate); according to the definitions of that document;

d) certain linkers described in patent U.S. Pat. No. 6,537,520, of formula

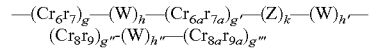

with: g+h+g'+k+h'+g"+h"+g'" other than 0; with the definitions identical to those of that document, column 8;

e) certain linkers described in document WO 02/085908 (with the definitions identical to those of that document), for example a linear or branched organic linking chain chosen from:
CR6'"R7'"-, (R6'")C=C(R7'")=, —CC—, —(O)—, —O—, —S—, —SOO—, —N(R3'")-, —(R6'") C=N—, —C(S)—, —P(OO(OR3'")-, —P(O)—(OR3444)O—, with R'"3 being a group capable of reacting with a nitrogen or an oxygen, a cyclic region (divalent cycloalkyls, divalent heterocyles), polyalkylenes, polyalkylene glycols;

f) linkers of document WO 03/011115, pages 124-125;

g) linkers of document US 2006/0018830.

The choice of Linker (structure and size) may be made in particular so as to control the charge, the lipophilicity or the hydrophilicity of the product of formula (I), in order to optimize the biological targeting or the biodistribution. Use may in particular be made of linkers which are biodegradable in vivo, or PEG or mini-PEG linkers. The choice of the linker is made in such a way as not to impair the effectiveness of the compound of formula (I) according to the invention, a test which makes it possible to verify this effectiveness in vitro being presented in the detailed description.

According to another embodiment, the term "signal" represents a marker for optical imaging (fluorescent molecule used in optical imaging, in particular a compound known to have a maximum absorption or emission between 450 and 1500 nm). Dyes representing the Signal entity and suitable for optical imaging are known to those skilled in the art and are, for example, chosen from the following or derivatives thereof: cyanines, merocyanines, indocyanines, phthalocyanines, naphthalocyanines, triphenylmethines, porphyrins, pyrilium, thiapyrilium, squarylium, croconium, azulenium, indoaniline, benzophenoxazinium or benzothiaphenothiazinium dyes, anthraquinones, napthoquinones, indathrenes, phthaloylacridones, traphenoquinories, azo dyes, tropones, tetrazines, fe(dithiolene) dyes, fos(benzene-dithioate) dyes, iodoaniline dyes, 6/s(S,O-dithiolene) dyes, chomophores, in particular fluorescein, sulforhodamine 101 (Texas Red), rhodamine B, rhodamine 6G, rhodamine 19, indocyanine, Cy2, Cy3B, Cy3.5, Cy5, Cy5.5, Cy7 and Cy7.5. Mention may in particular be made of the following structures:

| Type | Structure |
| --- | --- |
| Fluorescein | 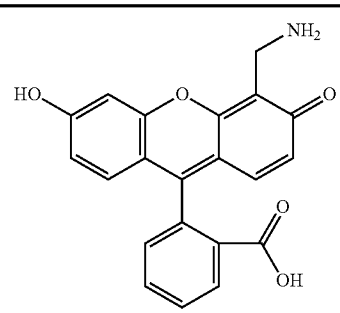 |

| Type | Structure |
|---|---|
| Rhodamine | 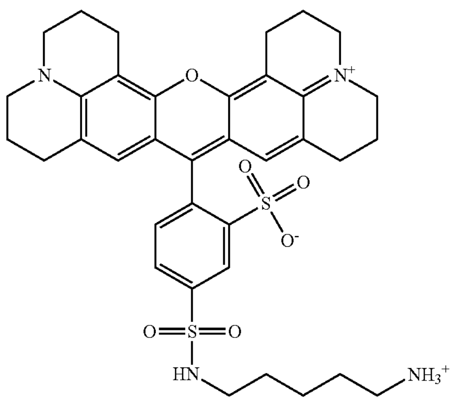 [SMILES: [NH3+]CCCCCNS(=O)(=O)c1ccc(C2=c3cc4c5c(c3Oc3c2cc2c6c3CCCN6CCC2)CCC[N+]=5CCC4)c(S(=O)(=O)[O-])c1] |
| Cyanine | |
| Cyanine | |

According to another embodiment. Signal represents quantum dots (inorganic fluorophores comprising nanocrystals).

According to another embodiment. Signal represents a superparamagnetic nanoparticle coated with an organic layer, commonly denoted SPIO or USPIO ("ultra small particles of iron oxide"). Advantageously, the nanoparticle comprises a core of iron oxide or hydroxide, in particular of magnetite ($Fe_3O_4$) or of maghemite ($\gamma$-$Fe_2O_3$). Use will advantageously be made of a nanoparticle covered with a citrate, silane, siloxane, phosphate, phosphonate, bisphosphonate, advantageously gem-bisphosphonate, coating, described in WO200458275 (and other variants of such coatings, for example, described in WO2007095871, WO2007064175, WO2007099289, US20090208420, WO2008115854), the particle and the method of coupling between the peptide and the nanoparticle being detailed in the examples of the present application. The magnetic nanoparticles used are very advantageously nanoparticles based on an iron compound and covered with a layer comprising one or more identical or different gem-bisphosphonate compounds, the layer covering the nanoparticle having the following formula (C):

$$\text{T-L2-CH(PO}_3\text{H}_2)_2 \qquad (C)$$

in which:
the linker L2 represents an organic group linking the T function to the gem-bisphosphonate —$CH(PO_3H_2)_2$ function;
T represents a chemical function coupled to the MUC5AC PEPTIDE or to the linker of the present application. In one particular embodiment, T-L2 represents the Linker of the compound of formula (I).

The composition is in the form of a stable aqueous solution of nanoparticles. In these compositions, the degree of complexation of the compound (C) on the particles is greater than 50%, advantageously greater than 70% and preferably greater than 80%, 90%, 95% (the phosphonate component binds to the metal core). Particularly preferably, the acidic magnetic particles (p) are complexed on at least 90% of their protonated sites with compounds of formula (C), some of these compounds C being coupled to MUC5AC PEPTIDES. According to one variant, some of the T functions of the layer are coupled to an MUC5AC PEPTIDE, and some of the T functions are coupled to a hydrophilic compound, in particular a compound bearing hydroxyl groups, and in particular an aminoalcohol hydrophilic compound denoted AAG3AA28, described in WO2004058275 (example 8), or a PEG group.

The magnetic particles (p) have a hydrodynamic diameter of between 5 and 300 nm, preferably between 5 and 60 nm and more preferably between 5 and 30 nm.

The linker L2 makes it possible to link and/or space apart the gem-bisphosphonate function and the reactive entity T capable of providing the covalent grafting of the MUC5AC PEPTIDE (the biovector) on the nanoparticle, optionally by means of the Linker.

Preferably, the linker L2 represents a divalent group.
Preferably, the linker L2 is chosen from:
an aliphatic; alicyclic; aliphatic alicyclic; aromatic; or aliphatic aromatic group, it being possible for said aliphatic, alicyclic and aromatic groups to be optionally substituted with a methyl, hydroxyl, methoxy, acetoxy or amido group, or a halogen atom, advantageously a chlorine, iodine or bromine atom;
a group —$l_1$—NHCO—$l_2$, wherein $l_1$ and $l_2$, which may be identical or different, represent an aliphatic; alicyclic; aromatic; aliphatic alicyclic or aliphatic aromatic group, it being possible for said groups to be optionally substituted with a methyl, hydroxyl, methoxy, acetoxy or amido group or a chlorine, iodine or bromine atom.

According to preferred implementations, L2 represents a substituted or unsubstituted aliphatic group, and more preferentially a —$(CH_2)_p$— group, wherein p is an integer from 1 to 5, or preferentially a —$(CH_2)_n$—NHCO—$(CH_2)_m$— group, wherein n and m represent an integer from 0 to 5.

In the light of the application, those skilled in the art understand that the number of chemical linking groups forming the linking component is variable depending on the type of compounds I. For example:
when the Signal is a chelate intended to be coupled to a single Peptide, the linking component is advantageously a chemical group linking the chelate and the Peptide;
when the Signal is a chelate multimer intended to be coupled to a Peptide, the linking component is advantageously a chemical group linking the multimer to the Peptide as is known to those skilled in the art;
when the Signal is a nanoparticle, in particular a metal nanoparticle such as a nanoparticle of metal oxide covered with numerous (typically a few hundred to a few thousand) MUC5AC PEPTIDE molecules, each MUC5AC PEPTIDE is grafted to the metal oxide core via a chemical linking group as is known to those skilled in the art;
when the Signal is a lipid nanoparticle in emulsion, in the form of a lipid nanodroplet in emulsion formed by an aqueous core coated with a lipid layer of surfactants on which MUC5AC PEPTIDES (several hundred to several thousand) are anchored, each of these MUC5AC PEPTIDES is grafted to this lipid layer via a chemical linker.

The biological tests described in detail in the application make it possible to select effective peptides which are equivalent or improved in terms of MUC5AC-targeting activity in comparison with the peptides exemplified in detail in the present application.

The invention also relates to a diagnostic method using a compound of formula (I) as previously described.

The present invention also relates to a composition comprising at least one compound of general formula (I) as previously described, advantageously intended for parenteral administration.

The invention also relates to the use of a compound according to the present invention for the diagnosis or the preparation of a composition for diagnosis of an MUC5AC-related pathological condition, in particular chosen from hereditary colorectal diseases (in particular familial adenomatous polyposis (FAP) and Lynch syndrome), and chronic inflammatory bowel diseases, in particular in individuals who have been affected for many years (ulcerative colitis and Crohn's disease), populations at risk of contracting colorectal cancer, follow-up of recurrences in patients who have already been treated for colorectal cancer, and advantageously among individuals with a high risk of developing colorectal cancer and follow up of recurrences of colorectal cancer.

Advantageously, the physiological conditions which promote a risk of colorectal cancer are chosen from hereditary colorectal diseases associated with the formation of colorectal adenomatous polyps, chronic inflammatory bowel disease (IBD), and individuals over the age of 50 of both sexes and with a 1st-degree family history of colorectal adenoma or cancer. Advantageously, the follow-up of recurrence of colorectal cancer is chosen from: individuals with a personal history of developed adenomas or of cancer before the first procedure.

For an MRI diagnosis, the intravenous administration by injection, usually in saline solution, is typically carried out at a metal ion dose of from 0.001 to 1.5 mmol/kg of body weight, for example from 1 to 500 µmol Gd/kg. For a radiopharmaceutical diagnosis, the intravenous administration by injection, usually in saline solution, is typically carried out at a dose of from 1 to 100 mCi for 70 kg of body weight, preferably from 5 to 50 mCi, with diagnostic imaging, for example, 30 to 180 minutes after the injection for $^{99}$Tc.

It is recalled that, for MRI, the metal is typically a paramagnetic metal, the paramagnetic metals including lanthanides with an atomic number of 58-70 and transition metals with an atomic number of 21-29, 42 or 44, for example scandium, titanium, vanadium or chromium. Advantageously, the paramagnetic metal is chosen from the elements: manganese, iron, cobalt, nickel, copper, molybdenum, ruthenium, cerium, praseodymium, neodymium, promethium, samarium, europium, gadolinium, terbium, dysprosium, holmium, erbium, thulium and ytterbium. The elements Gd(III), Mn(II), europium and dysprosium, advantageously Gd, are particularly preferred. In the case of use in multimodal imaging (for example MRI+PET) or in nuclear medicine (SPECT and/or PET imaging), the chelates can be used for complexing a radioelement such as, in particular, $^{99}$Tc, $^{117}$Sn, $^{111}$In, $^{97}$Ru, $^{67}$Ga, $^{68}$Ga, $^{89}$Zr, $^{177}$LU, $^{47}$SC, $^{105}$Rh, $^{188}$Re, $^{60}$Cu, $^{62}$CU, $^{64}$CU, $^{67}$CU, $^{90}$Y, $^{159}$Gd, $^{149}$Pr or $^{166}$Ho, preferably technecium, indium or gallium.

For use as X-ray contrast agents, the concentration of heavy atom is typically from 0.1 M to 5 M, with concentrations via intravenous administration of about from 0.5 to 1.5 mmol/kg. According to another aspect, the invention relates to the use of a compound (I) as previously described, for preparing a composition intended for optical imaging.

Examples of administrations of a composition for medical imaging are described in the prior art, for example in document WO 0226776 and US 2006/0018830, column 36 ([0282]), section 8 (dosages and additives).

Pharmaceutically physiologically acceptable vehicles for forming diagnostic compositions (contrast product) comprising the compounds previously described are known from the prior art. Use will, for example, be made of salts (sodium, calcium, meglumine) and pH-controlling agents (acetic acid, citric acid, fumaric acid, antioxidants).

The invention also relates to a process for preparing compounds comprising the coupling of an MUC5AC PEPTIDE with at least one chelate. Several general methods for preparing compounds of formula (I) that are described in US 2006/0018830 (Bracco) are applicable by using a Peptide in the place of the peptides of those documents. These methods, chosen according to in particular the chelate chosen, are recalled in 2006/0018830, column 37 ([0288] to [0291]) ("general preparation of compounds", and "alternative preparation of the compounds via segment coupling"), for example the SPPS and FMOC (9-fluorenylmethyl carbamate) methods. The invention also relates to a method of diagnosis which comprises administering a compound (I), carrying out an imaging examination using appropriate equipment, and analyzing the results.

The invention covers, unless otherwise indicated, all the chiral, diastereoisomer and racemic forms, in particular cis-trans, and L-D forms, of the compounds described.

The applicant has studied the possibilities of combination of an MUC5AC PEPTIDE coupled to several chelates in the compound of formula (I). The applicant has, moreover, studied compounds of formula (I) exhibiting an assembly between one or more MUC5AC-targeting Peptides of the compound of formula (I), and one or more chelates, in such a way that the access to the target is not impaired despite the presence of the chelate(s). For example, the chelate is spaced apart from the PEPTIDE(S) P by the Linker which has a sufficient size and a chemical structure such that the recognition of the peptide(s) by their target is not impaired. Among the biovector (peptide or possible other biovector)/chelate combinations, mention may in particular be made of:

a central biovector peptide linked to several identical or different chelates, a central chelate linked to several identical or different peptides, a first [peptides bearing chelate(s)] assembly coupled by means of a hydrophobic or hydrophilic linker to a second [peptide bearing chelates] assembly, written for example:

Ch1-peptide1-Linker-peptide2-Ch2 with Ch representing identical or different chelates and peptide1 and peptide2 representing identical or different Peptides, a peptide1-(Linker bearing Ch)-peptide2-Ch assembly.

Use will, for example, be made of the method for contraction of multimeric compounds that is described in US2005/0100963 (WO2006/031885, page 66, line 25 to page 69, line 30) in the case of peptides targeting KDR receptors (for example by means of method 13 of the examples: "preparation of homodimers and heterodimers"), but using the MUC5AC PEPTIDE (the peptides of the compounds of FIGS. 44 to 47 of US20050100963 will, for example, be replaced with MUC5AC PEPTIDES). The compound can thus advantageously comprise a peptide coupled to several chelates, or a chelate coupled to several peptides which are identical or different.

It will be possible, where appropriate, to couple the peptide component or the chelate component to chemical groups which makes it possible to promote biodistribution, for the lifetime of the product in the blood.

The specificity of the product refers to its ability to bind to the MUC5AC mucin target, the binding specificity typically being. Kd and Ka constants, the Kd value for the target markers preferably being about or less than 100 µM, preferably less than 10 µM, more preferably less than 1 µM and advantageously from 1 to 100 nM.

Definitions:

The definitions of pathological conditions of which the diagnosis is the subject of the present invention are reiterated here.

The term "MUC5AC-targeting peptide" or "MUC5AC PEPTIDE" denotes a molecule capable of selectively binding to MUC5AC.

The term "colorectal tumors and precancerous lesions" includes in particular the states marking the development of a colorectal polyp and the complications ensuing from a neoplastic polyp and/or from its progression toward the formation of a colorectal tumor.

"Hereditary colorectal diseases" are pathological conditions which increase the susceptibility to developing colon cancer and which are induced by mutations carried by the genomic DNA of the individual. Hereditary colorectal diseases essentially group together familial adenomatous polyposis and Lynch syndrome (HNPCC: Hereditary nonpolyposis colorectal cancer).

A "polyp" is a raised formation jutting out from the intestinal mucosa which most commonly is not responsible for digestive symptoms; various types of polyps exist: neoplastic polyps (which can lead to cancer) and nonneoplastic polyps (which do not lead to cancer). Among the neoplastic polyps, adenomatous polyps represent 70% to 75% of colorectal polyps and are classified in 3 types according to their microscopic appearances: tubular adenoma, tubulovillous adenoma and villous adenoma.

"Adenomatous polyp or adenoma" denotes a delimited seat of epithelial dysplasia corresponding to abnormalities of the cells of the colonic mucosa. The frequency of adenomas increases with age. The macroscopic appearance of an adenoma may be sessile, pediculed or flat.

"Dysplasia" is a malformation or deformation resulting from an abnormality of the development of a tissue or of an organ.

"Chronic inflammatory bowel diseases" denote a set of chronic inflammatory lesions, of unknown cause, which can affect the small intestine, the colon and the rectum. These affections have varied clinical manifestations and often a relatively unpredictable chronic progression. This groups together ulcerative colitis and Crohn's disease. The inflammatory lesions are secondary to activation of the intestinal immune system upstream of which the environmental factors (lifestyle, intestinal microorganisms, viruses) and genetic factors (predisposition) have not yet been clearly identified.

In the present application, the following table of correspondence is used.

| Alanine | A | Ala |
| Arginine | R | Arg |
| Asparagine | N | Asn |
| Aspartate | D | Asp |
| Cysteine | C | Cys |
| Glutamate | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As illustrated later, the applicant has demonstrated the effectiveness of products for MRI comprising a chelate linked to the MUC5AC PEPTIDE, in particular CPSIYPLLC (SEQ ID No: 2).

Thus, even if a peptide was known from the prior art, the identification of its usefulness in a mechanism for targeting MUC5AC, among the extremely large number of possible biological targets, is far from obvious. Furthermore, it is in no way obvious that, this biological target identified, coupled compounds (MUC5AC PEPTIDE-signal entity) make it possible to solve the technical problems solved by the applicant, in particular:

- the preservation of the affinity, under physiological conditions, for the biological recognition site, despite the steric hindrance and the possible conformational modification in vivo owing to the coupling to a signal entity;
- the possibility of chemical coupling with the signal entities;
- the physicochemical stability in vivo, which constitutes a major limitation for numerous peptides;
- the ability to be recognized in imaging under physiological conditions in particular in vitro, in particular in MRI, a technique in which the level of sensitivity is close to 1000 times lower than PET imaging.

Overall, it was absolutely not obvious:
- on the one hand, for those skilled in the art to select the peptides which are the subject of the present invention;
- on the other hand, for the products integrating these peptides to be actually effecting under physiological conditions.

Detailed examples of implementations of the invention illustrated by means of the following figures are now described.

Figure 1:
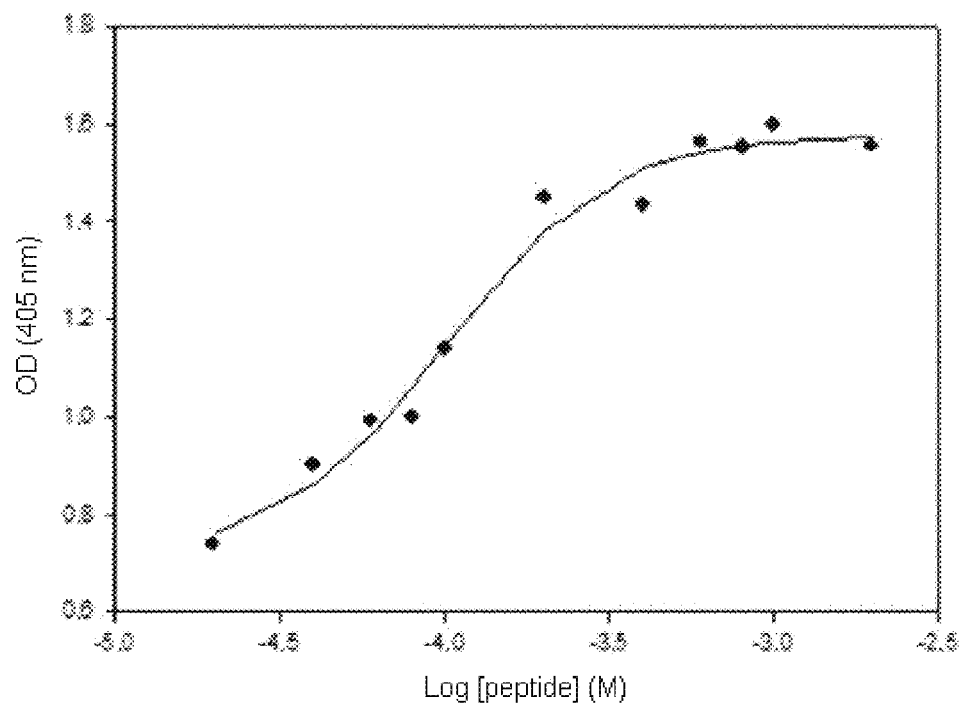
FIGS. 1, 2 and 3 illustrate the calculation of the Kd* (apparent dissociation constant) value of the peptide for human colonic MUC5AC, for murine (rat and mouse) gastric MUC5AC and for MUC5AC directly after secretion on secretory human adenocarcinoma cells, respectively.

FIGS. 6A to D and 7A to D represent the variation in the signal as percentage ΔSI (tumor or stomach or liver or spleen/reference) in RARE analysis as a function of time in minutes, of mice:

- bearing an MUC5AC-positive tumor, signal in the tumor after injection of 20 μmol/kg of PEG750-C60c (n=3) (FIG. 6A),
- bearing an MUC5AC-positive tumor, signal in the tumor after injection of 20 μmol/kg of control compound (n=5) (FIG. 6B),
- bearing an MUC5AC-negative tumor, signal in the tumor after injection of 20 μmol/kg of PEG750-C60c (n=4) (FIG. 6C),
- bearing an MUC5AC-positive tumor, signal in the stomach after injection of 20 μmol/kg of control compound (n=2) (FIG. 6D),
- bearing an MUC5AC-positive tumor, signal in the liver after injection of 20 μmol/kg of PEG750-C60c (n=3) (FIG. 7A), bearing an MUC5AC-positive tumor, signal in the aver after injection of 20 μmol/kg of control compound (n=3) (FIG. 7B), bearing an MUC5AC-negative tumor, signal in the liver after injection of 20 μmol/kg of PEG750-C60c (n=2) (FIG. 7C), bearing an MUC5AC-positive tumor, signal in the spleen after injection of 20 μmol/kg of control compound (n=2) (FIG. 7D).

EXAMPLES PART I

Preparation of the Compounds Including MUC5AC Peptides

General Information
M: Molar concentration (mol/l).
M/z: Mass to charge determined by mass spectrometry.
ES$^+$: Positive-mode electrospray,
ES$^-$: Negative-mode electrospray.
kDa: Unit of molecular weight (kiloDalton)
TLC: Thin Layer Chromatography
Z aye: Hydrodynamic diameter measured by PCS
Assaying of Total Iron:
The iron is assayed by atomic absorption spectroscopy (Varian AA10 spectrophotometer) after mineralization with concentrated HCl and dilution relative to a calibration range of ferric ions (0, 5, 10, 15 and 20 ppm).
Particle Size:
Hydrodynamic Diameter of the Drafted Particle (Z Ave):
Determined by PCS (Malvern 4700 instrument, laser 488 nm at 90°) on a sample diluted to ~1 millimolar with water for injection filtered through 0.22 μm.
PCS=Photon Correlation Spectroscopy=dynamic light scattering technique—Reference: R. Pecora in *J. of Nano. Res.* (2000), 2, p 123-131.
Structural Analyses:
By mass spectroscopy (Micromass VG Quattro II instrument) with an electrospray source.
Relaxivity Measurements:
The relaxation times T1 and T2 were determined by standard procedures on a Minispec 120 instrument (Bruker) at 20 MHz (0.47 T) at 37° C. The longitudinal relaxation time T1 is measured using an inversion recovery sequence and the transverse relaxation time T2 is measured using a CPMG technique.
The relaxation rates R1 (=1/T1) and R2 (=1/T2) were calculated for various concentrations of total metal (ranging from $0.1\times10^{-3}$ to $1\times10^{-3}$ mol/l) in aqueous solution at 37° C. The correlation between R1 or R2 as a function of the concentration is linear, and the slope represents the relaxivity r1 (R1/C) or r2 (R2/C) expressed as (1/second)×(1/mmol/l), i.e. ($mM^{-1}\cdot s^{-1}$).

The nanoparticles were prepared according to the methods described in patent WO2004/058 275 (US 2004/253181), examples 8 and 9 for the preparation of the colloidal solutions of magnetic particles, and examples 10 to 12 for the complexation of the magnetic particles with a gem-bisphosphonate coating of example 1 of WO2004/058 275.

The particularly advantageous peptide sequences are given in the following table:

| No. | Code | Peptide | Sequence |
|---|---|---|---|
| 1 | Cyclic C60 | 8-Amino-3,6-dioxaoctanoyl-cyclo-[Cys-Pro-Ser-Ile-Tyr-Pro-Leu-Leu-Cys]-NH$_2$ | CPSIYPLLC (SEQ ID NO: 2) |
| 2 | C60 | 8-Amino-3,6-dioxaoctanoyl-Pro-Ser-Ile-Tyr-Pro-Leu-Leu- NH$_2$ | PSIYPLL (SEQ ID NO: 3) |
| 3 | C16 | 8-Amino-3,6-dioxaoctanoyl-cyclo-[Cys-Ala-Leu-Ile-Pro-Pro-Leu-Leu-Cys]-NH$_2$ | CALIPPLLC (SEQ ID NO: 5) |

Example I.1

Coupling of the Peptides to the Iron Oxide Particle

Coupling of Peptide No. 1 to an Iron Oxide Particle
Protocols:

| No. | Code | Peptide | Sequence |
|---|---|---|---|
| 1 | Cyclic C60 | 8-Amino-3,6-dioxaoctanoyl-cyclo-[Cys-Pro-Ser-Ile-Tyr-Pro-Leu-Leu-Cys]-NH$_2$ | CPSIYPLLC (SEQ ID NO: 2) |

Coupling:

15 ml of nanoparticles ([Fe]=0.338 M) are stirred at ambient temperature, the pH is equal to 7.2. A solution of the peptide (No. 1, 20 mg) in 1 ml of water is added in portions of 100 μl with 2.25 mg of EDCI every 15 minutes. At the end of the addition, the solution is kept stirring overnight. The pH is adjusted to 7 with a 0.1M NaOH solution.

The solution is then filtered through 0.22 μm (Millipore® Durapore filter) and ultrafiltered on a 30 kDa membrane, and then concentrated to a final volume of 15 ml.

PEG Coupling:

2.5 ml of a solution of 1.060 g of amino-PEG (O-(2-aminoethyl)-O'-methylpolyethylene glycol 750. Aldrich, RN [80506-64-5]) in 5 ml of water are added to 15 ml of the previous solution. The pH of the solution is adjusted to 8 with 1M HCl and then 0.325 g of EDCI is added and the mixture is stirred for 3 h. The addition of the solution of amino-PEG (2.5 ml) and of EDCI (0.325 g) is repeated once and the mixture is stirred at ambient temperature overnight. The pH is brought back to 7.5 with 1M HCl. The solution is filtered through 0.22 μm and ultrafiltered on a 30 kDa membrane. The final volume of solution is 15 ml.

Characterization:

PCS: Z ave=28 nm; iron concentration: 240 mM $r_1$ (20 MHz, 37° C.): 30.54 $s^{-1}mM^{-1}$ $r_2$ (20 MHz, 37° C.): 96·$s^{-1}mM^{-1}$ $r_1$ (60 MHz, 37° C.): 14.94 $s^{-1}mM^{-1}$ $r_2$ (60 MHz, 37° C.) 95.06 $s^{-1}mM^{-1}$

| Samples | Magnetic diameter | Magnetization at saturation (magn.). |
|---|---|---|
| PEG750-C60c | 7.2 nm | 70 Am²/Kg |

Example I.2

Coupling of the Peptides to a Gadolinium Chelate (for Use in MRI)

(the use of squarate is described, but it is clear that the invention covers any linker such as the alkylene and/or PEG groups cited in the application)

General scheme:

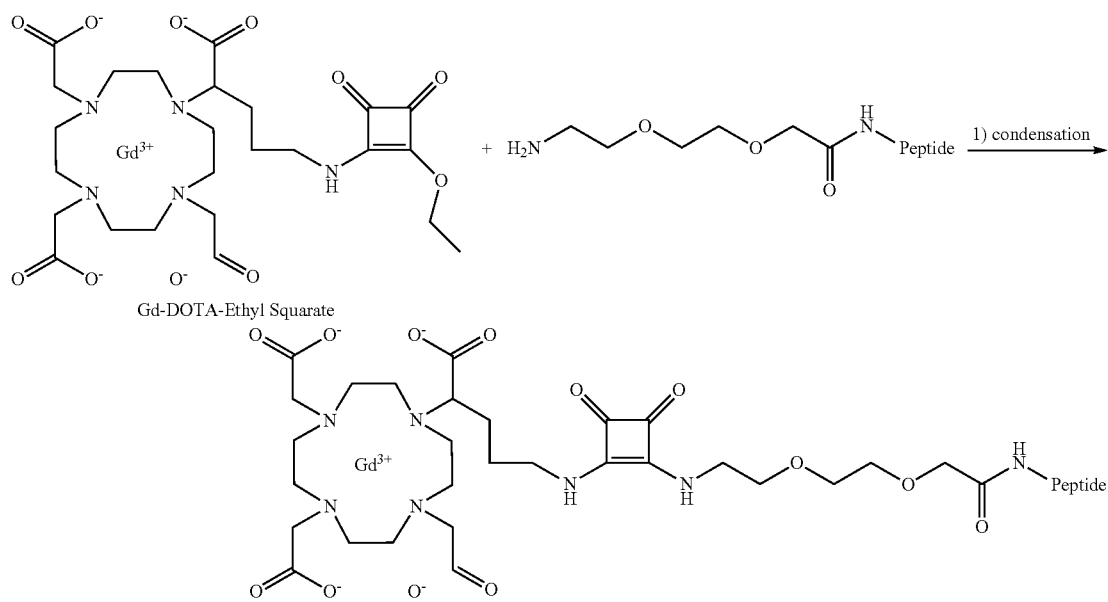

Gd-DOTA-Ethyl Squarate

Sequence of the Peptides Coupled:

| No. | Code | Peptide | Sequence |
|---|---|---|---|
| 1 | Cyclic C60 | 8-Amino-3,6-dioxaoctanoyl- cyclo-[Cys-Pro-Ser-Ile-Tyr-Pro- Leu-Leu-Cys]-NH₂ | CPSIYPLLC (SEQ ID NO: 2) |

Condensation, Deprotection:

200 mg of Gd-DATA-diethyl squarate (prepared according to WO2008125420) are dissolved in 20 ml of water. The pH is adjusted to 9 with a saturated $Na_2CO_3$ solution. 350 mg of peptide No. 1 are added and the pH is adjusted to 9.2. The mixture is left to react for 4 days. The solution is dialyzed on membranes with a cut-off threshold of 1000 Da for 48 h, and then chromatographed on an RP-18 column (eluent: MeOH/water (50/50)).

The product obtained has the following structure:

| No. | Structure | MW | Mass spectro. |
|---|---|---|---|
| 1 | 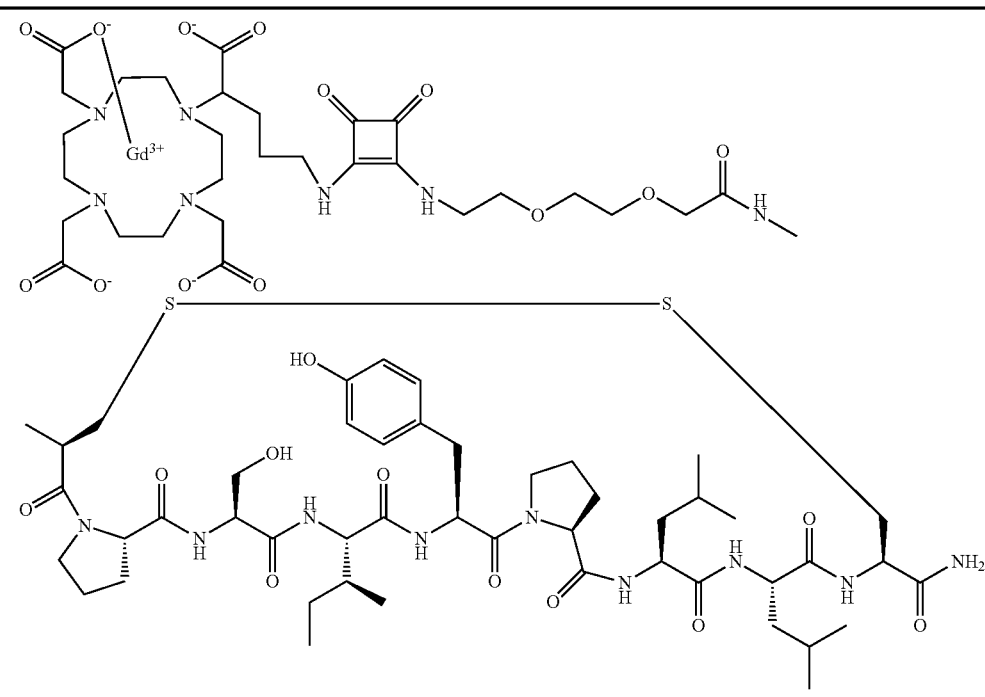 | 1843.20 | complies |
Example I.3
Coupling of the Peptide to a Chelate, the Product Obtained Complexing Gallium (Radionuclide for PET Imaging: Illustration with a Chelate of NOTA Type)

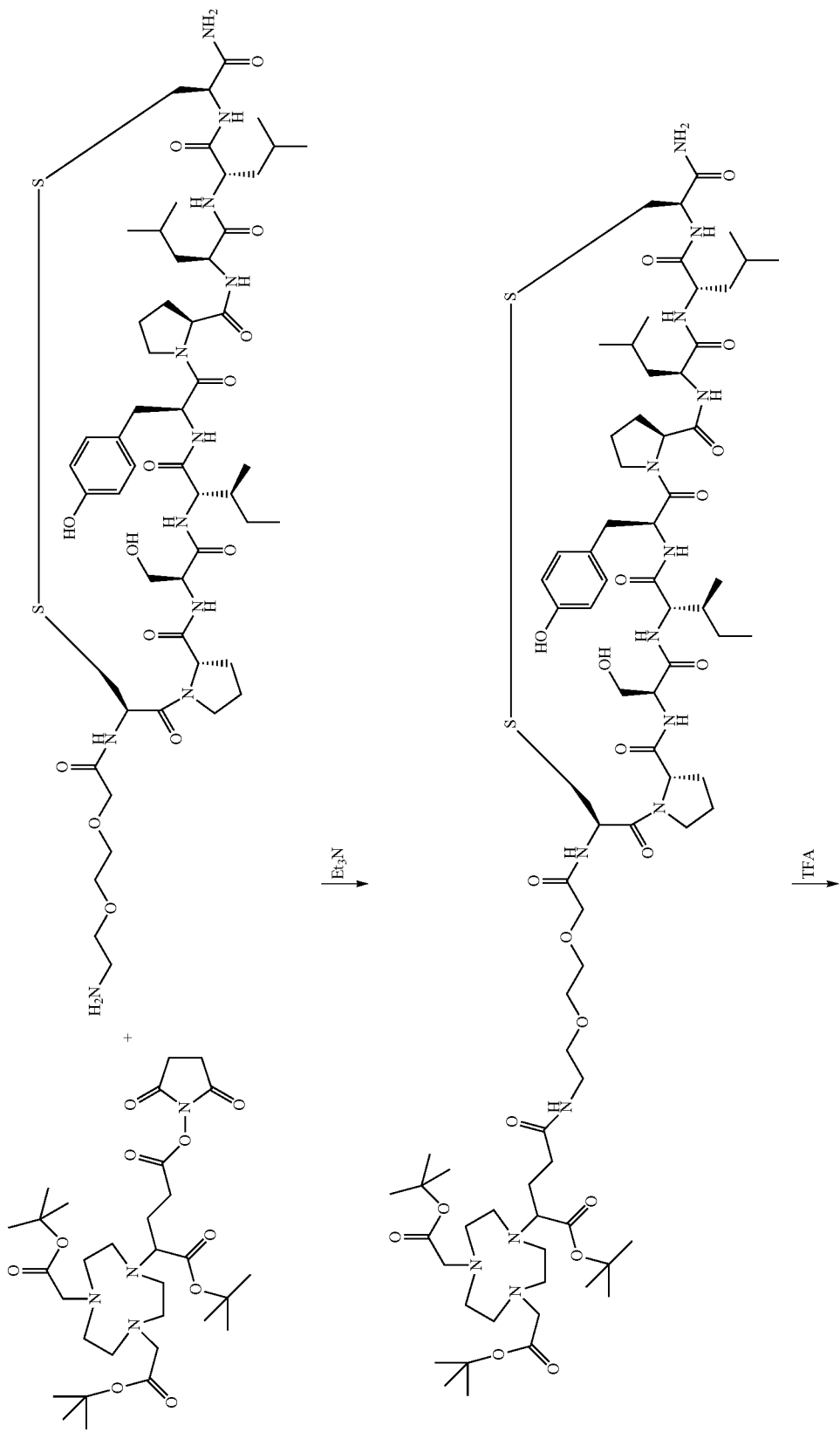

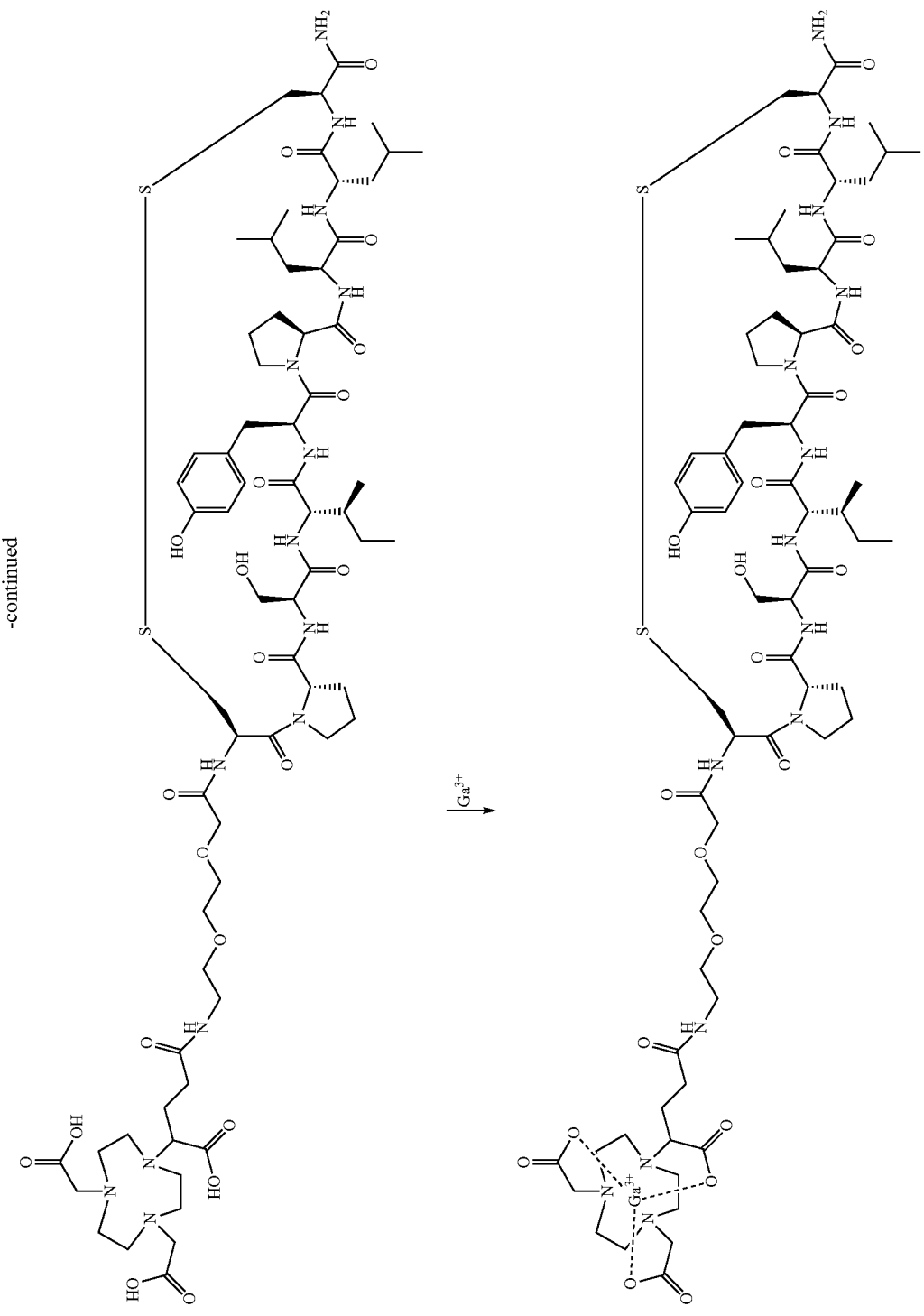

1—Formation of the Activated Ester:

NHS (1 equivalent) and then DCC (1 equivalent) are added to 100 mg (0.184 mmol) of NOTAGA(tBu)$_3$ (Chematech) in 3 ml of CH$_2$Cl$_2$. After reaction for half an hour at ambient temperature, the DCU formed is filtered through Whatman paper and the filtrate is concentrated to a final volume of approximately 0.5 ml.

2—Amidation:

Peptide No. 1 (1 equivalent) is dissolved in DMSO in the presence of 2 eq of NEt$_3$. The activated ester, in solution in CH$_2$Cl$_2$, is added.

After reaction for 2 H, the reaction medium is precipitated from 25 ml of Et$_2$O. After filtration, washing with Et$_2$O and drying under vacuum, white crystals are obtained. Yield=40%.

3—Deprotection

The resulting product is dissolved in TFA. After reaction for 7 H at ambient temperature, the TFA is evaporated off. The residue obtained is taken up in 4 ml of water. The product is purified on a C18 silica cartridge. 60 mg of product are obtained after freeze-drying.

4—Labeling

20 μg of the previously prepared compound (20 μl of a solution at 1 mg/ml) are dissolved in 2 ml of acetate buffer (pH 4), and 250 mBq of Ga$^{3+}$ resulting from the generator are added. The medium is stirred at ambient temperature for 10 min, and then purified on a Sep-Pak® C18 cartridge. The radiochemical purity obtained is 95 to 99% (3 tests).

Example I.4

Coupling of the Peptide to a Fluorescent Dye

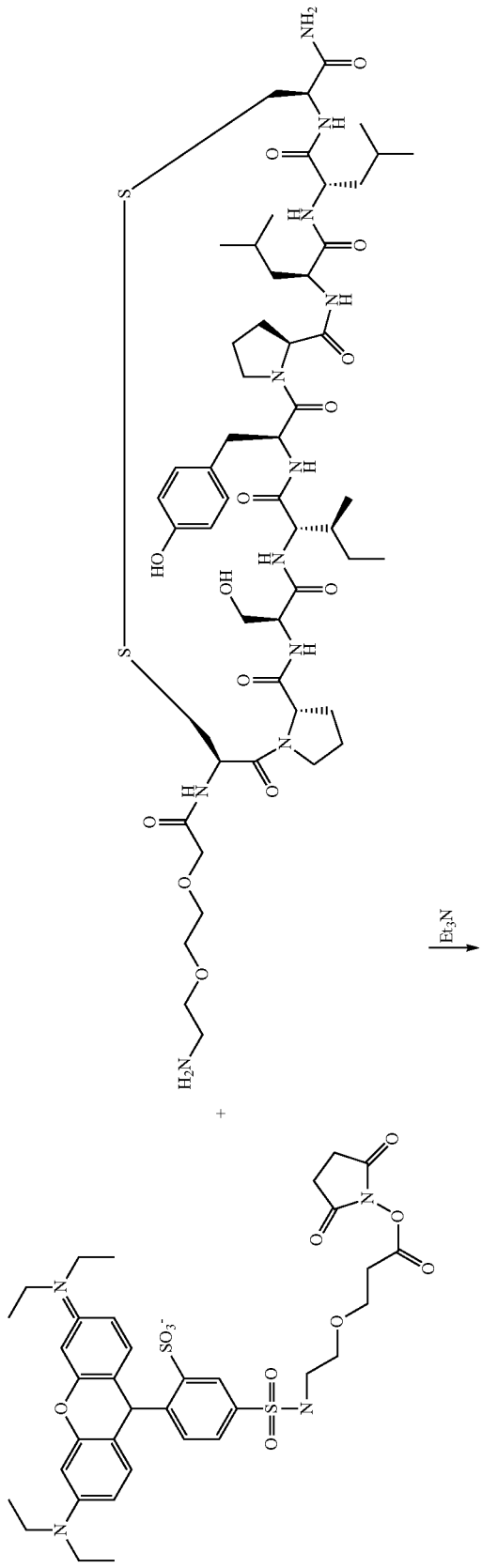

-continued
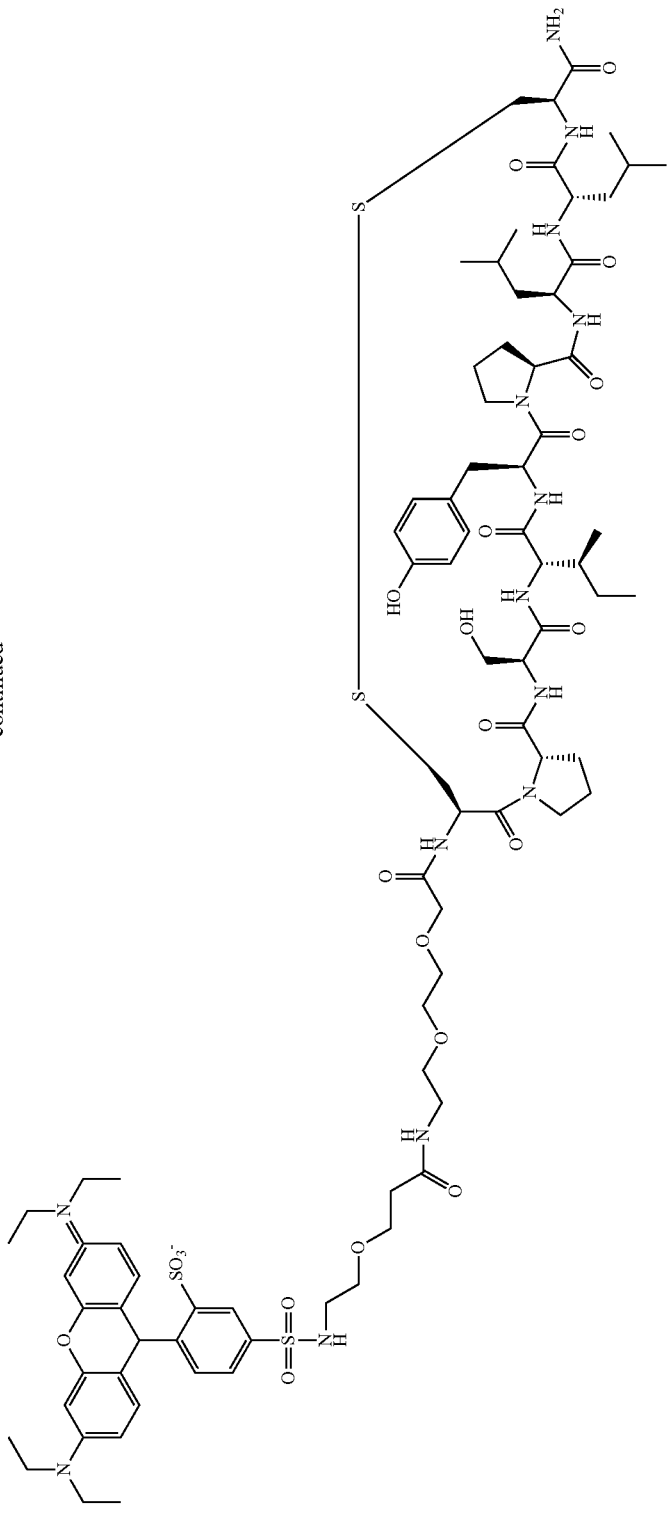

5 mg of SRB-EOP-SE dye (FluoProbes®) are added to a solution of 5 mg of peptide and 10 µl of triethylamine in 500 µl of DMSO. The mixture is stirred overnight at ambient temperature and in the dark. The reaction medium is precipitated from 20 ml of diethyl ether. The precipitate is recovered by centrifugation and rinsed twice with ether. After drying, the product is dissolved in water and purified by preparative HPLC on a C18 column (10×250 mm) using a water/acetonitrile/TFA (0.1%) eluent (gradient). After freeze-drying, the compound is stored at −20° C. MS: ES$^-$=1741.

EXAMPLES PART II

Product Characterization

Peptide CPSIYPLIC (SEQ ID No. 2)
Measurement of the Apparent Dissociation Constant on Human MUC5AC The interaction between the peptide and MUC5AC is evaluated by means of an ELISA assay. The mucin MUC5AC (purified from pieces of human tumor on the basis of mucin extraction and purification protocols described in literature) is immobilized on a plate at the concentration of 12.5 µg/ml overnight at 4° C. The nonspecific sites are then saturated in a buffer enriched with milk, for 2 hours at 4° C. After several rinses, the peptide CPSIYPLLC (SEQ ID No: 2) coupled to biotin is incubated at increasing concentrations ($10^{-3}$M and $10^{-6}$M) for 2 hours at 37° C. The biotinylated peptides bound to MUC5AC are visualized using goat anti-biotin antibodies incubated for one hour at ambient temperature and then diluted in PBS at 1 µg/ml. After removal of the unbound antibodies, a second incubation for one hour at ambient temperature is carried out in the presence of peroxidase-labeled anti-goat antibodies at 0.2 µg/ml, diluted in PBS supplemented with 0.1% of Tween-20. The peroxidase coloration reaction is carried out in the presence of $H_2O_2$-enriched ABTS. The measurement of the OD at 405 nm makes it possible to calculate the $K^*_d$ MUC5AC value. The interaction between the peptide and MUC5AC is also evaluated by means of the previously described ELISA assay on the mucin MUC5AC purified beforehand from mouse and rat stomach.

The affinity of the peptide for MUC5AC is calculated from a functional cell assay which consists in measuring the binding of the peptide on a cell model secreting MUC5AC. After 21 days of culture for HT29-5M21 cells and 7 days for HCT116 cells, the cells are rinsed with PBS at 4° C., and then fixed with 1% glutaraldehyde diluted in PBS. The cells are then rinsed again 3 times with PBS at 4° C. and incubated for 2 H at ambient temperature with a milk-enriched buffer and for 2 H at 37° C. in a concentration range of between $10^{-3}$M and $10^{-6}$M of biotinylated peptides. The biotinylated peptides bound to the target are visualized using goat anti-biotin antibodies incubated for one hour at ambient temperature (diluted in PBS to 1 µg/ml). A second incubation for one hour at ambient temperature is carried out in the presence of peroxidase-labeled anti-goat antibodies at 0.2 µg/ml, diluted in PBS supplemented with 0.1% of Tween-20. The peroxidase coloration reaction is carried out in the presence of ABTS and the OD measurement is carried out at 405 nm. The cell assay has the advantage of showing affinity data, although its sensitivity can still be improved. The secretion of MUC5AC was indeed verified in the study. The results on human tissues (affinity curve for human MUC5AC also obtained) give very positive results.

Evaluation of the Specificity on Tissue Sections

Figure 4:
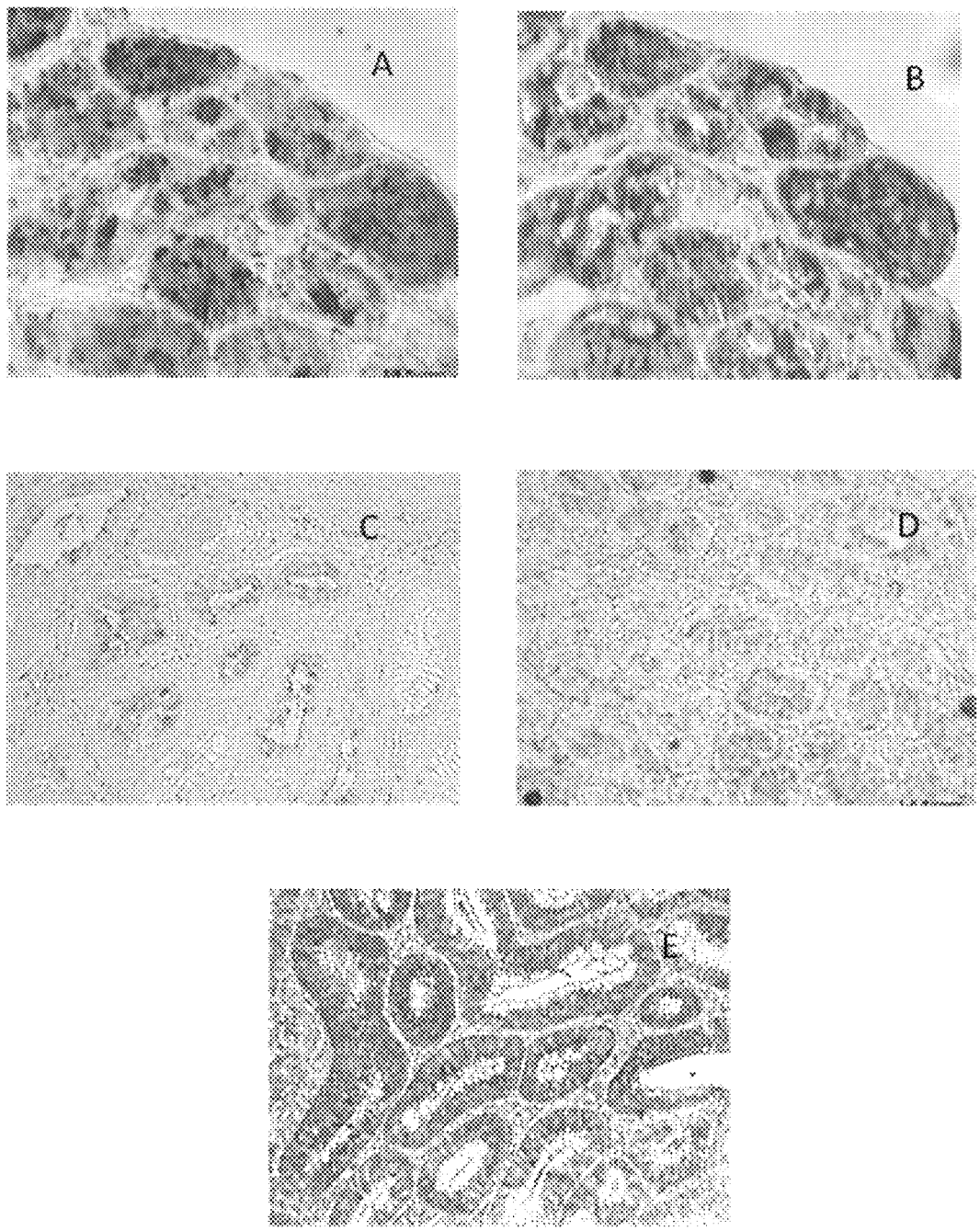
FIG. 4A shows an image of anti-MUC5AC and MUC2 antibody labeling of the peptide CPSIYPLLC (SEQ ID No. 2) on a section of healthy human gastric epithelium labeled with the biotinylated peptide CPSIYPLLC (SEQ ID No: 2) (magnification ×50).
FIG. 4B shows an image of anti-MUC5AC and MUC2 antibody labeling of the peptide CPSIYPLLC (SEQ ID No: 2) on a section of healthy human gastric epithelium labeled with anti-MUC5AC monoclonal antibodies (PM8, magnification ×50).
FIG. 4C shows an image of anti-MUC5AC and MUC2 antibody labeling of the peptide CPSIYPLLC (SEQ ID No: 2) on a section of the colonic adenoma labeled using the peptide CPSIYPLLC (SEQ ID No: 2) (magnification ×10), on tissues cut transversally.
FIG. 4D shows an image of anti-MUC5AC and MUC2 antibody labeling of the peptide CPSIYPLLC (SEQ ID No: 2) on a section of the colonic adenoma labeled with anti-MUC5AC monoclonal antibodies, (PM8, magnification ×10), on sections cut transversally.
FIG. 4E shows an image of anti-MUC5AC and MUC2 antibody labeling of the peptide CPSIYPLLC (SEQ ID No: 2) on a section of the colonic adenoma labeled using anti-MUC2 polyclonal antibodies (magnification ×10), on tissues cut transversally.
Figure 5:
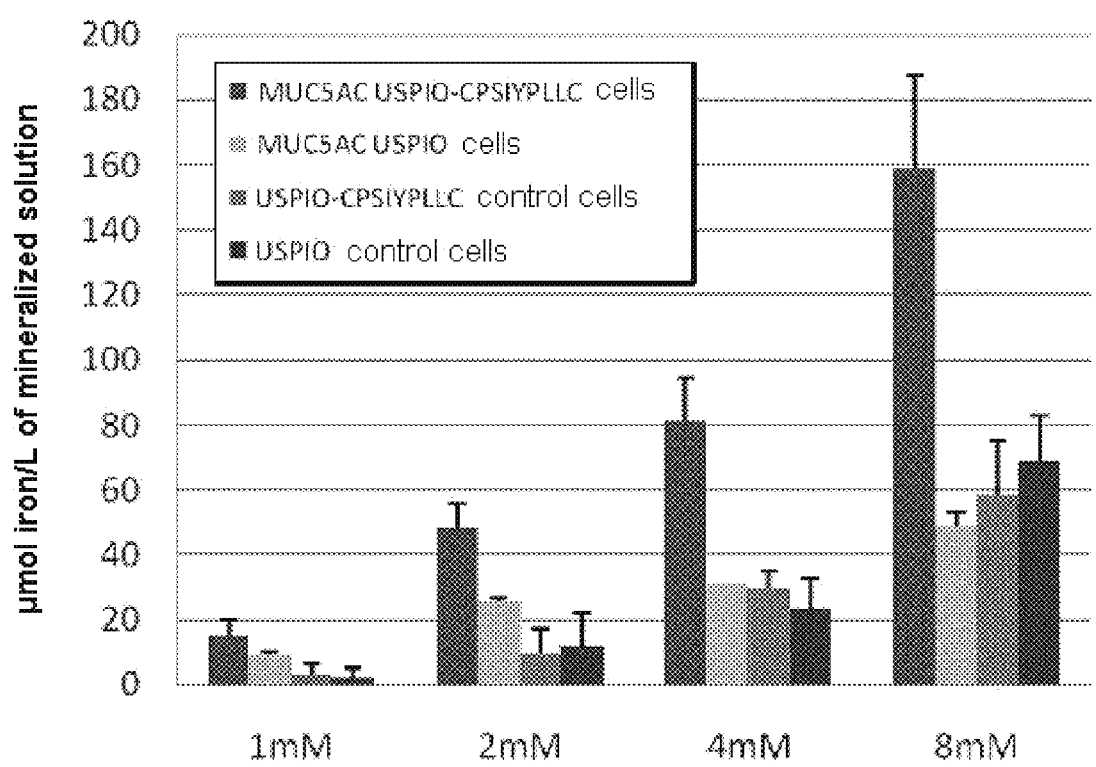
FIG. 5 represents the amount of iron directly correlatable to the binding of USPIO-CPSIYPLLC (SEQ ID No: 2) and of USPIO alone on two human colonic adenocarcinoma cell lines, with a line secreting MUC5AC (MUC5AC cells) and a line not secreting MUC5AC (control cells).

Sections of healthy gastric and colonic mucosae and of human colorectal adenoma (5 µm thick) were fixed for 24 h with 4% paraformaldehyde and embedded in paraffin. For the labeling, the sections were first of all deparaffinized in toluene and rehydrated in 95% alcohol. After rinsing in water, the slides are brought to boiling for 10 minutes in a citrate buffer (50 mM, pH 4). Once the temperature of the buffer has returned to 25-30° C., the slides are then rinsed with PBS and then successively incubated for 15 minutes in a 0.15% hydrogen peroxide ($H_2O_2$) solution and a kit for blocking the endogenous biotin for 1 h. The sections are then blocked using a milk-enriched buffer for 1 h at ambient temperature, and are then incubated at 4° C. for 18 h with the peptides at various concentrations (20 µM, 10 µM, 1 µM, 0.2 µM, 0.04 µM) or the antibodies (MUC5AC: PM8 at a 1/100 dilution and MUC2: Lum2-3 at a 1/100 dilution) diluted in PBS. The biotinylated peptides bound to the target are visualized using goat anti-biotin antibodies incubated for one hour at ambient temperature and then diluted in PBS at 1 µg/ml. A second incubation for one hour at ambient temperature is carried out in the presence of peroxidase-labeled anti-goat antibodies at 0.2 µg/ml diluted in PBS supplemented with 0.1% of Tween-20. The anti-MUC5AC and anti-MUC2 antibodies are visualized using an anti-mouse and anti-rabbit secondary antibody, respectively, each coupled to peroxidase and diluted to 1/250. After various washes in PBS, the slides are incubated with 0.05% DAB (3,3'-diaminobenzidine tetrahydrochloride) supplemented with 0.015% of $H_2O_2$, for 50 minutes. The various sections used (FIG. 4) are of healthy human gastric epithelium labeled with the biotinylated peptide CPSIYPLLC (SEQ ID No: 2) (magnification ×50) (A), with anti-MUC5AC monoclonal antibodies, (PM8, magnification ×50) (B), but also of the colonic adenoma labeled using the peptide CPSIYPLLC (SEQ ID No: 2) (magnification ×10), on tissues cut transversally (C), with anti-MUC5AC monoclonal antibodies, (PM8, magnification ×10), on sections cut transversally (D), and using anti-MUC2 polyclonal antibodies (magnification ×10), on tissues cut transversally (E).

USPIO-CPSIYPLLC (SEQ. ID No: 2) Contrast Product Test on Colonic Cell Models

After 21 days of culture for HT29-5M21 cells (MUC5AC cells), the literature reports that MUC5AC is massively expressed. HCT116 cells do not express MUC5AC (control cells). The cells are rinsed with PBS at 4° C. and then directly brought into contact with 0.5 ml of USPIO diluted in PBS, for 1 H at 37° C. (incubator, 5% $CO_2$). The USPIOs are tested at various iron concentrations of 1/2/4/8 mM on each of the lines. After the supernatant has been drawn off, the cells are washed twice with PBS and then scraped so as to subsequently be taken up with 250 µl of PBS (twice). The suspensions are subsequently freeze-dried and then taken up with 100 µl of a 5N HCl solution for 4 H at 80° C. in a water bath. The assay is then carried out using Paris reagent, before carrying out the relaxometry (Bruiser Minispec 60 MHz). The secretion of MUC5AC by the HT29 model and the absence of secretion with HCT116 were verified in the study.

References

Gouyer V, Wiede A, Buisine M P, Dekeyser S, Moreau O, Lesuffleur T, Hoffmann W and Huet G (2001) Specific secretion of gel-forming mucins and TFF peptides in HT-29 cells of mucin-secreting phenotyp, Biochim. Biophys. Acta. 1539: 71-84.

Sheehan J K, Brazeau C, Kutay S, Pigeaon H, Kirkham S, Howard M and Thornton D J (2000) Physical characterization of the MUC5AC mucin: a highly oligomeric glycoprotein whether isolated from cell culture or in vivo from respiratory mucous secretions, Biochem. Journal. 347: 37-44.

EXAMPLES PART III

Biological Tests

III.1 Peptide CPSIYPLLC (SEQ ID No. 2)

Figure 2:
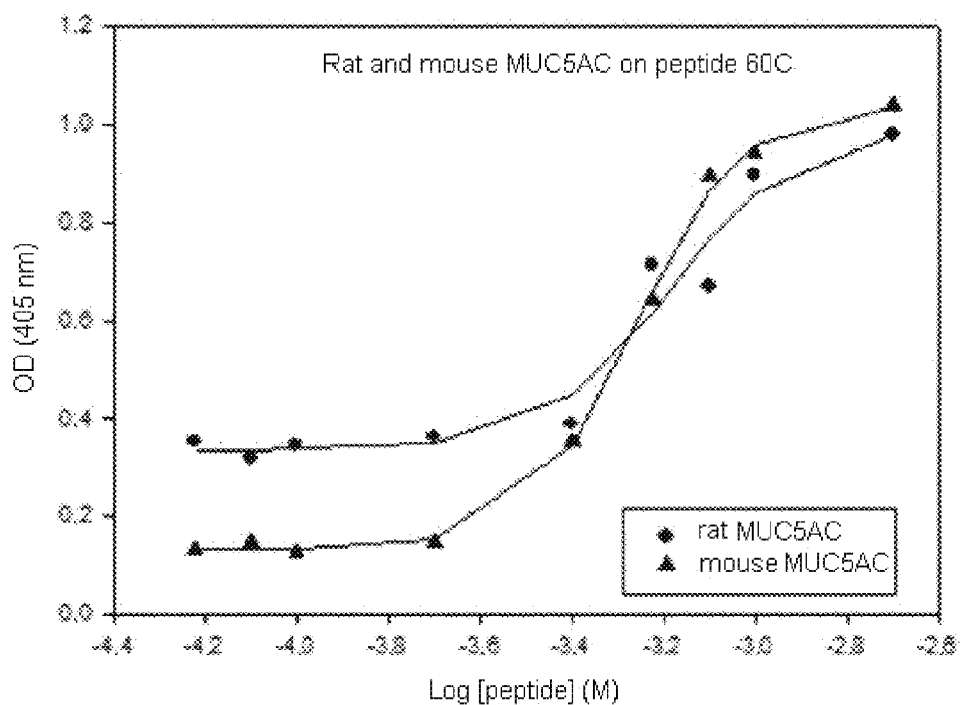

The ELISA assay (FIG. 1) based on the immobilization of purified MUC5AC in the presence of increasing concentrations of the peptide CPSIYPLLC (SEQ ID No: 2) makes it possible to calculate an apparent dissociation constant $K^*_d$ value equal to $8.5 \times 10^{-5}$ M, which demonstrates the good interaction between the peptide and the human MUC5AC molecule. The apparent dissociation constant $K^*_d$ values are $6.59 \times 10^{-4}$ M and $5.49 \times 10^{-4}$ M between the peptide CPSIYPLLC (SEQ ID No: 2) and, respectively, the rat and mouse MUC5AC glycoprotein (FIG. 2), which indicates that the murine or rat models are models relevant for predicting the binding of the USPIO-CPSIYPLLC (SEQ ID No: 2) contrast product to the MUC5AC target.

Figure 3:
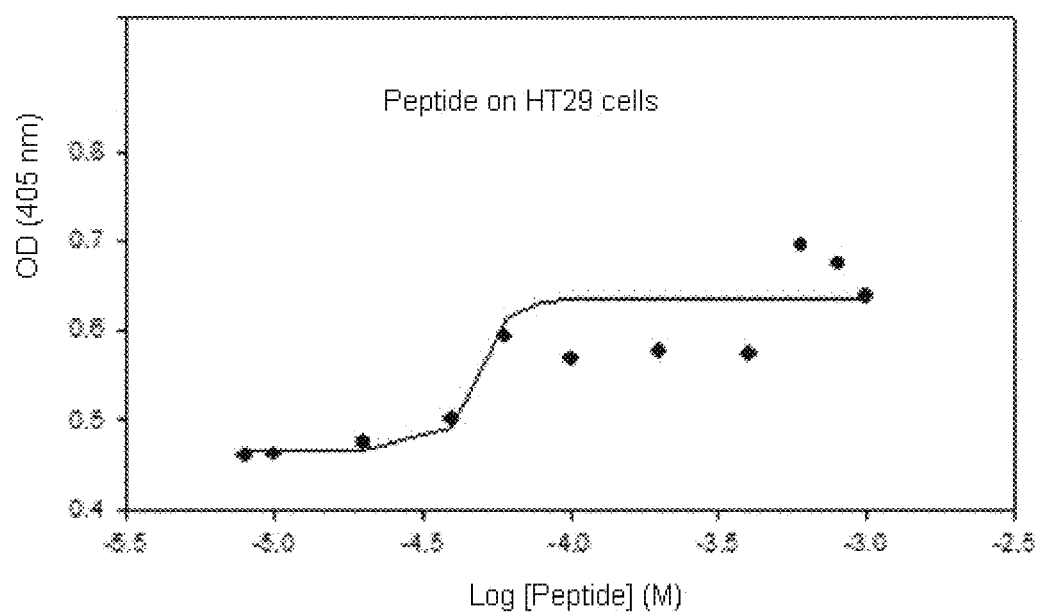

The test for binding of the peptide CPSIYPLLC (SEQ ID No: 2) on human colonic cancer cells (HT29 5M21) (FIG. 3) makes it possible to calculate an apparent dissociation constant $K^*_d$ value equal to $4.8 \times 10^{-5}$ M, which attests to the specific interaction between the peptide and native MUC5AC on live cells.

The labeling of sections of healthy human gastric epithelia (FIG. 4) makes it possible to demonstrate the specificity of the peptide, just like the labeling of sections of colonic adenoma which also indicate the absence of recognition, by the peptide CPSIYPLLC (SEQ ID No: 2), of the MUC2 glycoprotein which is the major mucin of the intestine.

III.2 USPIO-CPSIYPLLC (SEQ ID No: 2) Contrast Product

The iron concentration significantly increases on the MUC5AC cells in the presence of increasing concentrations of USPIO-CPSIYPLLC (SEQ ID No: 2). Conversely, in the presence of this same product, on the control cells, the concentration does not change proportionally to the concentration of USPIO-CPSIYPLLC (SEQ ID No: 2). Comparably, the USPIO without the peptide, whether on the MUC5AC cells or on the HCT116 cells (MUC5AC-negative), does not influence the iron concentration. It can therefore be deduced therefrom that USPIO-CPSIYPLLC (SEQ ID No: 2) is capable of binding to the MUC5AC cells. These results demonstrate that the grafting of the peptide CPSIYPLLC (SEQ ID No: 2) onto the USPIO makes it possible to specifically target MUC5AC secreted by human colonic adenocarcinoma cells, with a dose-response effect. There is specific targeting of MUC5AC, the specificity being observed for the highest concentrations, in particular 4 and 8 mM, of iron.

EXAMPLES PART IV

Imaging

In the experiments which follow, the following two compounds were used:
1) Compound according to the invention: PEG750-C60c of example I.1 above (peptide CPSIYPLLC (SEQ ID No: 2) coupled to an iron particle).
2) Control compound, which does not comprise the MUC5A-targeting peptide and was prepared as follows:
a) preparation of colloidal solutions of magnetic particles according to the methods described in examples 8 and 9 of application WO2004/058 275, then
b) complexation of the magnetic particles with a gem-bisphosphonate coating of example 1 of WO2004/058 275 according to the methods of examples 10 to 12 of application WO2004/058 275, then
b) coupling with PEG 750 according to the following protocol:

2.5 ml of a solution of 1.060 g of amino-PEG (O-(2-aminoethyl)-O'-methylpolyethylene glycol 750, Aldrich, RN [80506-64-5]) in 5 ml of water were added to 15 ml of nanoparticles ([Fe]=0.338 M) stirred at ambient temperature. The pH of the solution was adjusted to 8 with 1M HCl, then 0.325 g of EDCI was added and the mixture was stirred for 3 h. The addition of the solution of amino-PEG (2.5 ml) and of EDCI (0.325 g) was repeated once and the mixture was stirred at ambient temperature overnight. The pH was brought back to 7.5 with 1M HCl. The solution was filtered through 0.22 µm and ultrafiltered on a 30 kDa membrane. The final volume of solution was 15 ml.

IV.1 Molecular Magnetic Resonance Imaging (MRI)

The selected imaging parameters are the following:
RARE (rapid acquisition with relaxation enhancement) sequence (7T)
TR/TEeff=3000/48.7 ms,
RARE factor=4,
NEX=4,
Matrix=256×256
FOV=2.3 cm
slice thickness=1 mm
20 axial slices
spatial resolution=90 µm
acquisition time=12 min 48 s
Mice:
 bearing an MUC5AC-positive tumor were injected with PEG750-C60c (100 µmol/kg),
 bearing an MUC5AC-positive tumor were injected with the control compound (100 µmol/kg) and
 bearing an MUC5AC-negative tumor were injected with PEG750-C60c (100 µmol/kg).

The following results were observed on the MRI images of the tumors:
 The pre- and post-contrast MRI images of the MUC5AC-positive tumor treated with PEG750-C60c appear darker and a negative contrast image after injection of PEG750-C60c with a weak pixel intensity was therefore observed.
 Conversely, the MUC5AC-positive tumor treated with the control compound appears lighter and therefore has a positive contrast image with a strong pixel intensity.
 The effect observed in the MUC5AC-positive tumor treated with PEG750-C60c is not found in the mouse bearing an MUC5AC-negative tumor treated with PEG750-C60c, since no variation in contrast is observed in the tumor.

The stomach was also imaged since, in humans and rodents, it naturally possesses the mucin. MUC5AC. It was possible to observe, after injection of PEG750-C60c in the mice bearing an MUC5AC-positive or -negative tumor, a gastric region in contact with the lumen which exhibited a clear darkening delimited by the upper gastric tissue. This result clearly demonstrates the validity of PEG750-C60c for targeting the mucin MUC5AC. Indeed, using PEG750-C60c at equal concentration in animals having tumors with an opposite MUC5AC expression profile, but having the same mucin secretion characteristic in the stomach, a differential response was clearly observed in the tumor, but not in the stomach.

The MRI imaging experiments on the animals bearing xenografts are summarized in table 2.

TABLE 2

Summary of the number of mice imaged in the tumor during the two imaging campaigns.

|  | 100 µmol/kg | 20 µmol/kg |
|---|---|---|
| MUC5AC+ PEG750-C60c | 4 | 3 |
| MUC5AC+ control compound | 5 | 5 |
| MUC5AC− PEG750-C60c | 2 | 4 |

Figure 6:
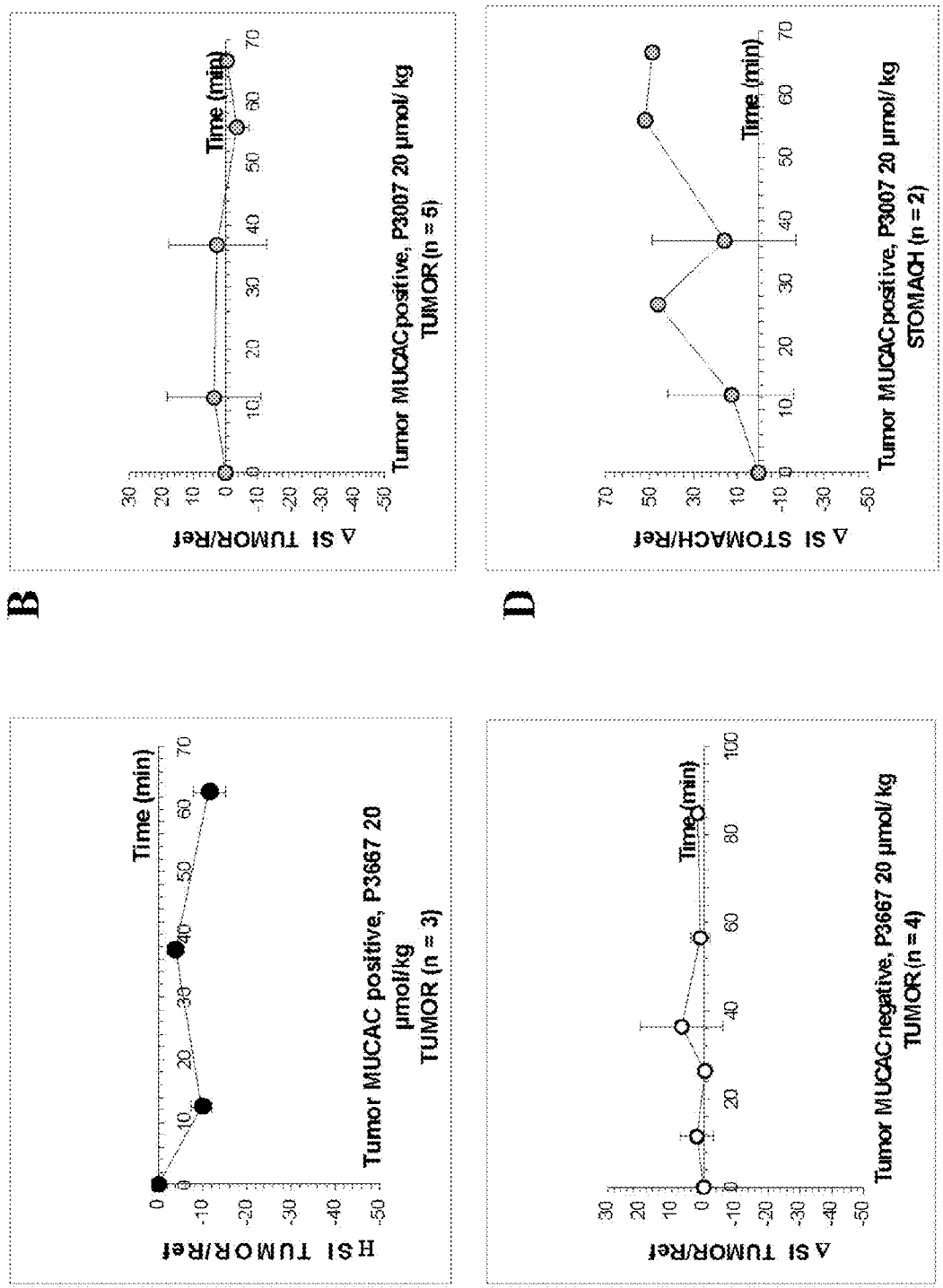
Figure 7:
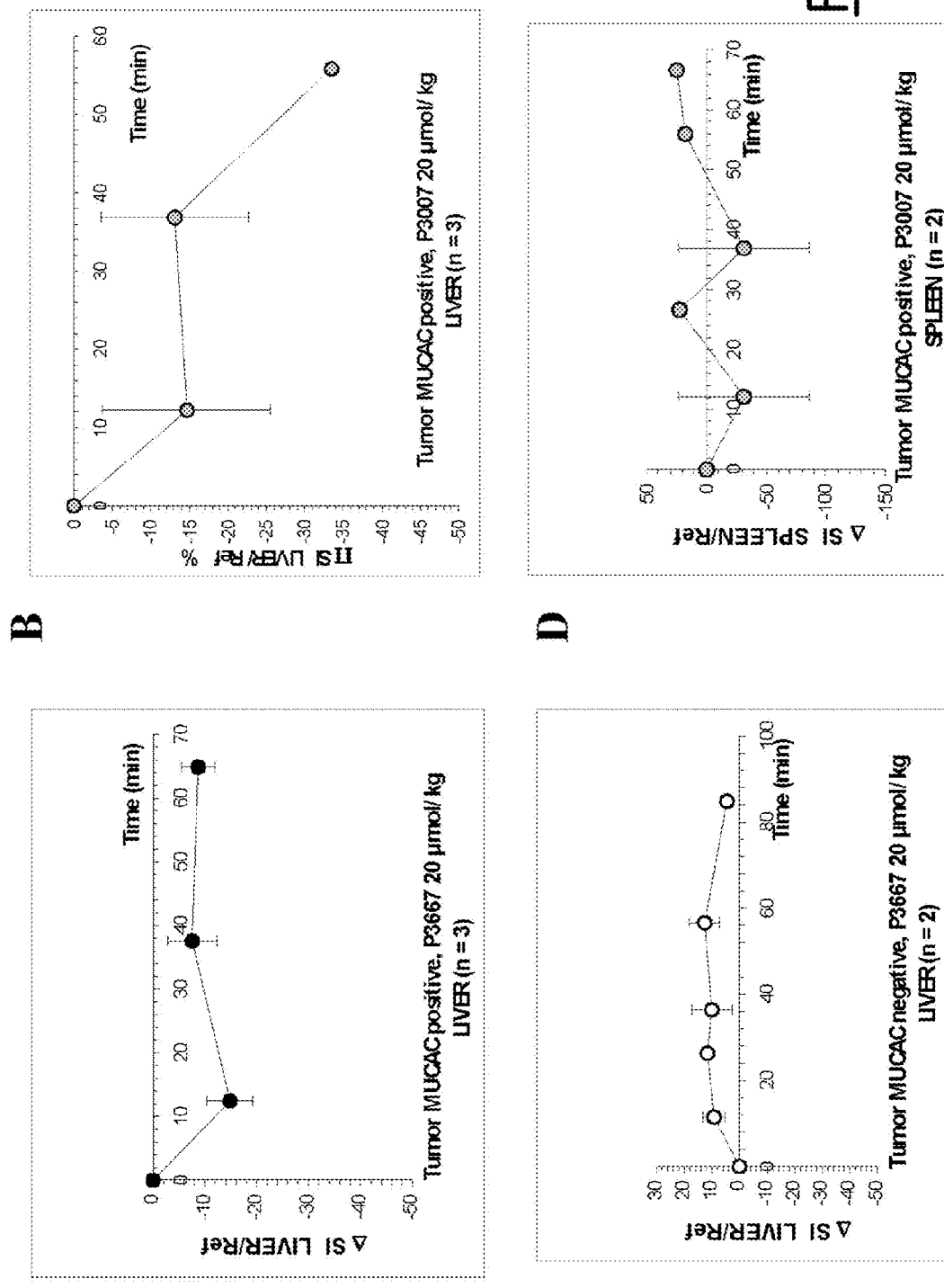

Whatever the dose of PEG750-C60c used, the MUC5AC-positive tumors exhibit a reproducible signal. The signal decreases between −10% (post-contrast) and −15% at respectively 20 µmol of iron/kg and 100 µmol of iron/kg (FIGS. 6 and 7). Under the same conditions, the two negative controls (PEG750-C60c/MUC5AC-negative and control compound/MUC5AC-positive) experience no change or a slight increase in their signal in the tumor.

It is observed in the stomach, after injection of PEG750-C60c at 100 µmol/kg, that there is a considerable decrease in signal of between −40% and −45%. Injection of the control compound lowers the signal in the stomach by −15%.

IV.2 Plasma Kinetics: Calculation of the Concentration of USPIO Contained in the Plasma of the Imaged Mice It can be observed in table 3 that the iron concentrations are proportional to the dose of product injected. Furthermore, the concentrations determined suggest that the products are only very slightly eliminated 1 h-1 h 30 after their injection.

TABLE 3

Iron concentration measured by relaxometry in the plasma of the mice

| Mice | Iron concentration (µmol/l) |
|---|---|
| 1 MUC5AC-positive PEG750-C60c 20 µmol Fe/kg | 380 |
| 2 MUC5AC-positive control compound 20 µmol Fe/kg | 411.5 |
| 3 MUC5AC-negative PEG750-C60c 20 µmol Fe/kg | 471.5 |
| 4 MUC5AC-positive PEG750-C60c 40 µmol Fe/kg | 909.6 |
| 6 MUC5AC-positive PEG750-C60c 20 µmol Fe/kg | 486.8 |
| 7 MUC5AC-positive PEG750-C60c 100 µmol Fe/kg | 1555.5 |
| 8 MUC5AC-positive control compound 100 µmol Fe/kg | 1804.8 |
| 9 MUC5AC-positive control compound 20 µmol Fe/kg | 306.4 |
| 10 MUC5AC-positive PEG750-C60C 20 µmol Fe/kg | 312.4 |
| 11 MUC5AC-negative PEG750-C60C 20 µmol Fe/kg | 442.5 |
| 12 MUC5AC-positive control compound 20 µmol Fe/kg | 334.4 |
| 13 MUC5AC-positive control compound 20 µmol Fe/kg | 343.3 |
| 14 MUC5AC-negative PEG750-C60C 20 µmol Fe/kg | 350.7 |
| 1 MUC5AC-positive PEG750-C60C 100 µmol Fe/kg | 2590 |
| 2 MUC5AC-positive control compound 100 µmol Fe/kg | 1883 |
| 3 MUC5AC-positive PEG750-C60C 100 µmol Fe/kg | 3871 |
| 4 MUC5AC-positive control compound 100 µmol Fe/kg | 1667 |
| 5 MUC5AC-positive PEG750-C60C 100 µmol Fe/kg | 1959 |
| 6 MUC5AC-positive control compound 100 µmol Fe/kg | 1781 |
| 7 MUC5AC-positive control compound 100 µmol Fe/kg | 1908 |
| 8 MUC5AC-positive control compound 20 µmol Fe/kg | 182 |
| 9 MUC5AC-negative PEG750-C60C 20 µmol Fe/kg | 337 |
| 10 MUC5AC-negative PEG750-C60C 100 µmol Fe/kg | 2806 |
| 11 MUC5AC-negative PEG750-C60C 100 µmol Fe/kg | 3638 |
| 12 MUC5AC-positive control compound 100 µmol Fe/kg | 2082 |

IV.3 Correlation Between the Imaging Results and the Animal Models

It can be observed in table 4, after anatornopathoiogical analysis, that all the tumors have an expected MUC5AC expression profile. Specifically, the xenografts performed with the line secreting MUC5AC (HT29 5M21) always express the mucin MUC5AC constantly, and the line which does not secrete it never expresses it. These results make it possible to validate the results observed by MRI analysis.

TABLE 4

Animals used and MUC5AC expression profile by histology

| Animals | Product injected | Dose (µmol/kg) | Cells | MUC5AC Immuno |
|---|---|---|---|---|
| Mouse 1 | PEG750-C60C | 20 | HT29 5M21 | + |
| Mouse 2 | Control compound | 20 | HT29 5M21 | + |
| Mouse 3 | PEG750-C60C | 20 | HCT116 | − |
| Mouse 4 | PEG750-C60C | 40 | HT29 5M21 | + |
| Mouse 6 | PEG750-C60C | 20 | HT29 5M21 | + |
| Mouse 7 | PEG750-C60C | 100 | HT29 5M21 | + |
| Mouse 8 | Control compound | 100 | HT29 5M21 | + |
| Mouse 9 | Control compound | 20 | HT29 5M21 | + |
| Mouse 10 | PEG750-C60C | 20 | HT29 5M21 | + |
| Mouse 11 | PEG750-C60C | 20 | HCT116 | − |
| Mouse 12 | Control compound | 20 | HT29 5M21 | + |
| Mouse 13 | Control compound | 20 | HT29 5M21 | + |
| Mouse 14 | PEG750-C60C | 20 | HCT116 | − |
| Mouse 1 | PEG750-C60C | 100 | HT29 5M21 | + |
| Mouse 2 | Control compound | 100 | HT29 5M21 | + |
| Mouse 3 | PEG750-C60C | 100 | HT29 5M21 | + |
| Mouse 4 | Control compound | 100 | HT29 5M21 | + |
| Mouse 5 | PEG750-C60C | 100 | HT29 5M21 | + |
| Mouse 6 | Control compound | 100 | HT29 5M21 | + |
| Mouse 7 | Control compound | 100 | HT29 5M21 | + |
| Mouse 8 | Control compound | 20 | HT29 5M21 | + |
| Mouse 9 | PEG750-C60C | 20 | HCT116 | − |
| Mouse 10 | PEG750-C60C | 100 | HCT116 | − |
| Mouse 11 | PEG750-C60C | 100 | HCT116 | − |
| Mouse 12 | Control compound | 100 | HT29 5M21 | + |

IV.4 Detection of USPIOs on Tissues after in vivo Injection in the Animal

An accumulation of PEG750-C60C could be observed in the tumors only when they secrete MUC5AC. Furthermore, it was possible to note specific labeling, and therefore an accumulation of PEG750-C60C in the mouse gastric tissue and an absence of labeling in the animals treated with the control compound.

In the experiments carried out, the PEG750-C60C was detected using the anti-PEG antibody on HT295M21 xenograft, on HCT116 xenograft and on a section of mouse stomach without counterstaining. The control compound was detected on a section of mouse stomach without counterstaining. The sections were visualized in parallel with an anti-MUC5AC antibody on HT295M21 and HCT116.

These results make it possible to validate the imaging analysis and to confirm the images obtained by MRI in the stomach of mice injected with the PEG750-C60C. indeed, it was possible to observe the appearance of signal in a layer indirectly in contact with the gastric lumen in the treated animals. It can therefore be concluded from this that the product does not accumulate as far as the upper part of the gastric epithelium, where, however, MUC5AC is also found. This can be explained by it being impossible for the USPIO to diffuse as far as the surface, by its deterioration at the acidic pH of the stomach or else by uptake by MUC5AC present in the bottom of the gastric crypts, thus preventing progression of the USPIOs.

The invention claimed is:

1. A compound and the pharmaceutically acceptable salts thereof, of the formula (I) Signal-Peptide or (II) Signal-Linker-Peptide, wherein:

Signal is a signal entity;
Linker is a chemical linking component; and
Peptide is a peptide consisting of a mucin 5A (MUC5AC)-targeting peptide,
wherein the MUC5AC-targeting peptide is selected from the group consisting of:
a) X1-X2-X3-X4-X5-X6-X7-X8-X9 (SEQ ID No: 1), wherein:

X1 is absent or cysteine or methionine,
X2 is hydroxyproline or proline,
X3 is threonine or serine,
X4 is isoleucine, leucine or valine,
X5 is tyrosine, phenylalanine or tryptophan,
X6 is hydroxyproline or proline,
X7 is isoleucine, leucine or valine
X8 is isoleucine, leucine or valine
X9 is absent or cysteine or methionine;
b) X10-X11-X12-X13-X14-X15-X16-X17-X18 (SEQ ID No: 4), wherein:

X10 is absent or cysteine or methionine,
X11 is isoleucine, leucine, valine or alanine, X12 is threonine or serine,
X13 is isoleucine, leucine or valine,
X14 is hydroxyproline or proline,
X15 is hydroxyproline or proline,
X16 is isoleucine, leucine or valine,
X17 is isoleucine, leucine or valine,
X18 is absent or cysteine or methionine; and
   c) CALIPPLLC (SEQ ID No: 5).

2. The compound and pharmaceutically acceptable salts thereof as claimed in claim 1, wherein the MUC5AC-targeting peptide is selected from the group consisting of CPSIYPLLC (SEQ ID No: 2), PSIYPLL (SEQ ID No: 3), and CALIPPLLC (SEQ ID No: 5).

3. The compound and pharmaceutically acceptable salts thereof as claimed in claim 1, wherein the Signal is a chelate coupled to a paramagnetic metal M.

4. The compound and pharmaceutically acceptable salts thereof as claimed in claim 1, wherein the Signal is a chelate.

5. The compound and pharmaceutically acceptable salts thereof as claimed in claim 3, wherein the chelate is selected from the group consisting of: 1,4,7,10-tetraazacycl dodecane-1,4,7,10-tetraacetic acid (DOTA), 2-[Bis[2-[bis(carboxymethyl)amino]ethyl]iamino]acetic acid (DTPA) 1,4,7,10-tetraazacyclododecane-1,4,7-triacetic acid (DO3A), 10-(2-hydroxypropyl)-1,4,7,10-tetraazacyclododecane-1,4,7-triacetic acid (HPDO3A), (9R,S)- 2,5,8-Tris(carboxymethyl)-12-phenyl-11-oxa-2,5,8-triazadodecane-1,9-dicarboxylic acid (BOPTA), 1,4,7-triazacyclononane-N,N', N"-triacetic acid (NOTA), 3,6,9,15-tetraazabicyclo[9.3.1]pentadeca-1(15),11,13-triene-3,6,9-triacetic acid (PCTA), 2-methyl-1,4,7,10-tetraazacyclododecane- 1,4,7,10-tetraacetic acid (MCTA), (α, α', α", α'")-tetramethyl-1,4,7,10-tetraazacyclododecane-1,4,7,10-tetracetic acid (DOTMA), 6-amino-6-methylperhydro-1,4-diazepine tetraacetic acid (AAZTA), Hydroxypyridinone (HOPO), and derivatives in which one or more carboxylic groups are in the form of a corresponding salt, ester, or amide; or a corresponding compound in which one or more carboxylic groups are replaced with a phosphonic and/or phosphinic group.

6. The compound and pharmaceutically acceptable salts thereof as claimed in claim 1, wherein the Linker comprises:
   a) Q1-1-Q2, in which Q1 and Q2, which may be identical or different, are O, S, NH, CO$_2$, —NHCO, CONH, NHCONH, NHCSNH, SO$_2$NH— or NHSO$_2$—, and 1 is an alkyl group, alkoxyalkyl group, polyalkoxyalkylene group, alkenyl group, alkynyl group, alkyl group interrupted with one or more squarates, with one or more aryls, or with one or more groups selected from the group consisting of —NH—, —O—, —CO—, —NH(CO)—, —(CO)NH—, —O(CO)— and —(OC)O—; or
   b) a group selected from the group consisting of:
      (CH$_2$)$_n$, (CH$_2$)$_n$—CO—, or —(CH$_2$)$_n$NH—CO— with n=2 to 10;
      (CH$_2$CH$_2$O)$_q$(CH$_2$)$_r$—CO— or (CH$_2$CH$_2$O)$_q$(CH$_2$)$_r$—NH—CO— with q=1-10 and r=2-10;
      (CH$_2$)$_n$—CONH—, (CH$_2$)$_n$—CONH—PEG, or (CH$_2$)$_n$—NH—, with n=1 to 5, or squarate;
      HOOC—CH$_2$—O—(CH$_2$)$_2$—O—(CH$_2$)$_2$—O—CH$_2$—COOH;
      HOOC—(CH$_2$)$_2$—CO$_2$—(CH$_2$)$_2$—OCO—(CH$_2$)$_2$—COOH;
      HOOC—CH(OH)—CH(OH)—COOH;
      HOOC—(CH$_2$)$_n$—COOH; NH$_2$—(CH$_2$)$_n$—NH$_2$, with n=1-20; and
      NH$_2$—(CH$_2$)$_n$—CO$_2$H; or NH$_2$—CH$_2$—(CH$_2$—O—CH$_2$)$_n$—CO$_2$H, with n=1 to 10.

7. The compound and pharmaceutically acceptable salts thereof as claimed in claim 1, wherein the Signal is an ultrasmall particle of iron oxide coated with an organic layer.

8. The compound and pharmaceutically acceptable salts thereof as claimed in claim 7, wherein the organic layer is a gem-bisphosphonate layer.

9. The compound and pharmaceutically acceptable salts thereof as claimed in claim 1, wherein the Signal is a marker for optical imaging selected from the group consisting of cyanines, merocyanines, indocyanines, phthalocyanines, naphthalocyanines, triphenylmethines, porphyrins, pyrilium, thiapyrilium, squarylium, croconium, azulenium, indoaniline, benzophenoxazinium or benzothiaphenothiazinium dyes, anthraquinones, napthoquinones, indathrenes, phthaloylacridones, traphenoquinones, azo dyes, tropones, tetrazines, fe(dithiolene) dyes, fos(benzene-dithiolate) dyes, iodoaniline dyes, 6/s(S,O-dithiolene) dyes, and chromophores.

10. The compound and pharmaceutically acceptable salts thereof as claimed in claim 1, wherein the Signal is a lipid nanoparticle comprising at least one chelate.

11. A composition for medical imaging comprising at least one compound and the pharmaceutically acceptable salts thereof as claimed in claim 1 and a pharmaceutically acceptable excipient.

12. The compound and pharmaceutically acceptable salts thereof as claimed in claim 3, wherein the paramagnetic metal M is selected from the group consisting of Gd, Mn, Fe, Dy, and Tm.

13. The compound and pharmaceutically acceptable salts thereof as claimed in claim 4, wherein the chelate is coupled to a radionuclide selected from the group consisting of $^{99}$Tc, $^{177}$Sn, $^{111}$In, $^{97}$Ru, $^{67}$Ga, $^{68}$Ga, $^{89}$Zr, $^{177}$Lu, $^{47}$Sc, $^{105}$Rh, $^{188}$Re, $^{60}$Cu, $^{62}$Cu, $^{64}$Cu, $^{67}$Cu, $^{90}$Y, $^{159}$Gd, $^{149}$Pr, and $^{166}$Ho.

14. The compound and pharmaceutically acceptable salts thereof as claimed in claim 7, wherein the superparamagnetic nanoparticle coated with an organic layer comprises an iron oxide core.

15. The compound and pharmaceutically acceptable salts thereof as claimed in claim 10, wherein the chelate is selected from the group consisting of: DOTA, DTPA, DO3A, HPDO3A, BOPTA, NOTA, PCTA, DOTMA, AAZTA, HOPO, and derivatives in which one or more carboxylic groups are in the form of a corresponding salt, ester, or amide; or a corresponding compound in which one or more carboxylic groups are replaced with a phosphonic and/or phosphinic group.

16. A method for diagnosing a MUC5AC-related pathological condition comprising the steps of: (i) administering to a patient a compound of the formula (I) or (II) as claimed in claim 1; (ii) carrying out an imaging examination using MRI, X-ray, or optical imaging equipment; and (iii) analyzing the results of the imaging examination for the presence of MUC5AC in colonic mucosa.

17. The diagnostic method according to claim 16, wherein the pathological condition to be diagnosed is an MUC5AC-related pathological condition, selected from the group consisting of hereditary colorectal diseases, chronic inflammatory bowel diseases, populations at risk of contracting colorectal cancer, and follow-ups of occurrences in patients who have already been treated with colorectal cancer.

18. A compound and the pharmaceutically acceptable salts thereof, the compound comprising the structure:

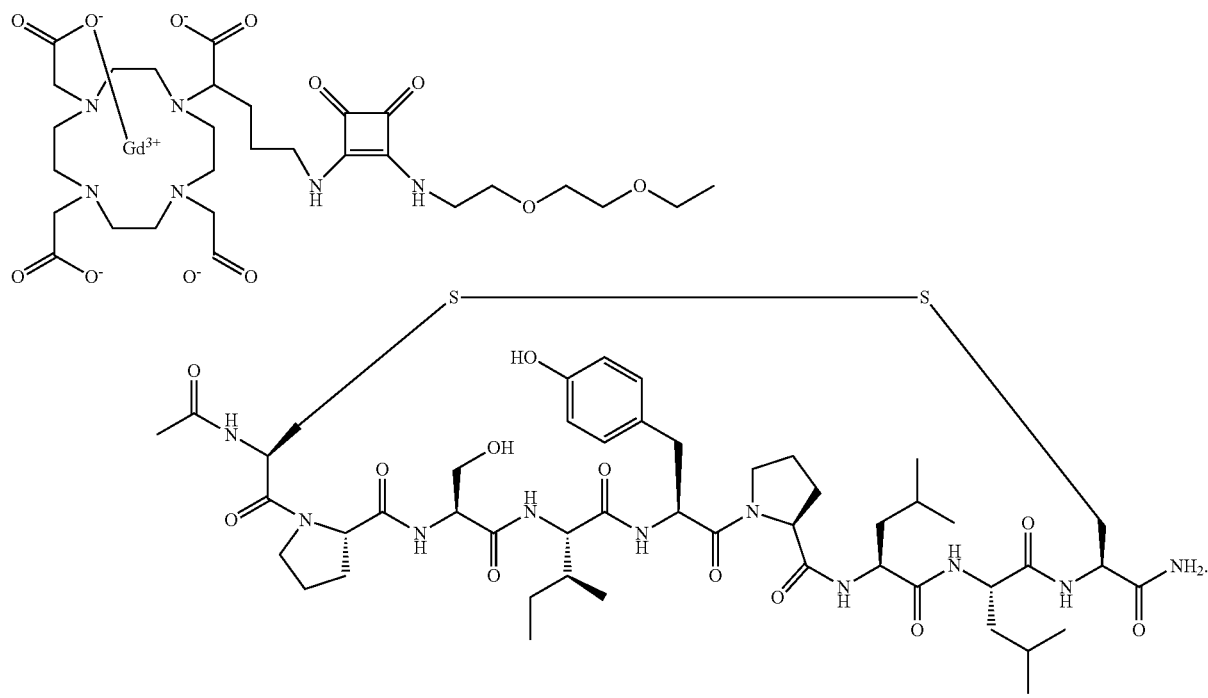
19. The compound and pharmaceutically acceptable salts thereof as claimed in claim 1, wherein the Signal is a marker for optical imaging having a maximum absorption or emission between 450 and 1500 nm.
20. The compound or pharmaceutically acceptable salt thereof of claim 5, wherein the chelate is:
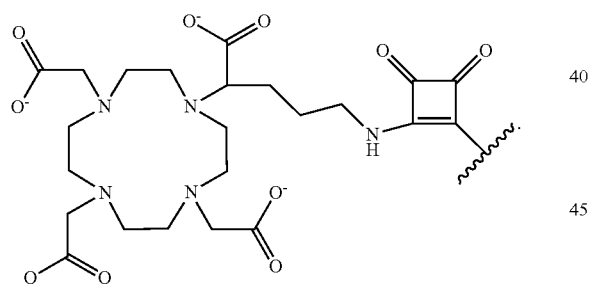
* * * * *